United States Patent

Riebel et al.

(10) Patent No.: US 6,348,435 B1
(45) Date of Patent: Feb. 19, 2002

(54) SUBSTITUTED 2,4-DIAMINO-1,3,5-TRIAZINE AND THEIR USE AS HERBICIDES

(75) Inventors: Hans-Jochem Riebel, Wuppertal; Stefan Lehr, Langenfeld; Uwe Stelzer, Burscheid, all of (DE); Markus Dollinger, Overland Park, KS (US); Mark Wilhelm Drewes, Langenfeld (DE); Randy Allen Meyers, Overland Park, KS (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/508,383

(22) PCT Filed: Sep. 24, 1998

(86) PCT No.: PCT/EP98/06098

§ 371 Date: May 1, 2000

§ 102(e) Date: May 1, 2000

(87) PCT Pub. No.: WO99/18100

PCT Pub. Date: Apr. 15, 1999

(30) Foreign Application Priority Data

Oct. 7, 1997 (DE) .......................... 197 44 232

(51) Int. Cl.$^7$ ...................... C07D 251/18; A01N 43/68
(52) U.S. Cl. ..................... 504/230; 544/207
(58) Field of Search ............... 504/232, 233, 504/230; 544/205, 206, 207

(56) References Cited

U.S. PATENT DOCUMENTS

| | | | |
|---|---|---|---|
| 2,961,377 A | 11/1960 | Shapiro et al. | 167/65 |
| 3,816,419 A | 6/1974 | Cross et al. | 260/249.9 |
| 3,932,167 A | 1/1976 | Cross et al. | 71/93 |
| 4,680,054 A | 7/1987 | Takematsu et al. | 71/93 |
| 4,844,731 A | 7/1989 | Takematsu et al. | 71/93 |
| 5,403,815 A | 4/1995 | Nishii et al. | 504/230 |

FOREIGN PATENT DOCUMENTS

| | | |
|---|---|---|
| DE | 2115318 | 12/1971 |
| EP | 0 411 153 | 2/1991 |
| EP | 0 581 960 | 2/1994 |
| JP | 63-222166 | 9/1988 |

OTHER PUBLICATIONS

J. Am. Chem. Soc., vol. 81, (month unavailable) 1959, pp. 3728–3736, Shapiro et al Hypoglycemic Agents. III. $N^1$–Alkyl– and Aralkylbiguanides.

Database WPI, Section Ch, Wk 8843, Derwent Publications Ltd., London, DB: Calss C02, AN 88–303295 XP002090401 & JP 63 22166 A (IDEMISU KOSAN CO LTD), Sep. 16, 1988.

Chemical Abstracts, vol. 120, No. 9, Feb. 28, 1994, Columbus, Ohio US; abstract No. 106941.

Kelarev V. I. et al; "Synthesis of N–substituted 2,4–diamino–1,3,5–triazines containing furfuryl groups", XP002090399 & Izv. Vyssh. Uchebn. Zaved., Khim Tekhnol., Bd. 36, Nr. 4, 1993, Seiten 33–39 Not found no month date.

Chemical Abstracts, vol. 071, No. 1, Jul. 7, 1969, Columbus, Ohio, US; abstract No. 0032454n.

Ishida N. et al: "1–Furfurylbiguanides" XP002090400, & JP 06 905218—(Sumitomo Chemical Co., Ltd.) Mar. 4, 1969.

*Primary Examiner*—John M. Ford
(74) *Attorney, Agent, or Firm*—Joseph C. Gil; James R. Franks; Jackie Ann Zurcher

(57) ABSTRACT

The invention relates to novel substituted 2,4-diamino-1,3,5-triazines of the formula (I)

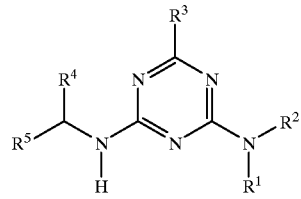

in which $R^1$ represents, for exampe, H or $C_1$–$C_6$-alkyl, $R^2$ represents, for example, H, $C_1$–$C_6$-alkyl or —CO—$R^6$, $R^3$ represents, for example, H, $C_1$–$C_6$-alkyl, $C_2$–$C_6$-alkenyl, $C_2$–$C_6$-alkinyl or $C_3$–$C_6$-cycloalkyl, $R^4$ represents, for example, H, $C_1$–$C_6$-alkyl or $C_3$–$C_6$-cycloalkyl, $R^5$ represents one of the groupings below,

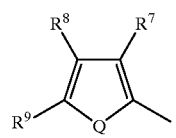 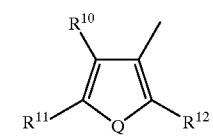

where $R^6$ represents, for example, $C_1$–$C_6$-alkyl, $C_1$–$C_6$-alkoxy or $C_2$–$C_6$-alkenyl, $R^7$ to $R^{12}$ represents, for example, H or certain organic radicals and Q represents O or S, to processes and novel intermediates for their preparation and to their use as herbicides.

15 Claims, No Drawings

SUBSTITUTED 2,4-DIAMINO-1,3,5-TRIAZINE AND THEIR USE AS HERBICIDES

This is a 371 National Application of PCT/EP98/06098, filed Sep. 24, 1998.

TECHNICAL FIELD OF THE INVENTION

The invention relates to novel substituted 2,4-diamino-1,3,5-triazines, to processes and novel intermediates for their preparation and to their use as herbicides.

BACKGROUND OF THE INVENTION

A number of substituted 2,4-diamino-triazines are already known from the (patent) literature (cf. JP 63222166—cited in Chem. Abstracts 111:97288w; cf. also U.S. Pat. Nos. 3,816,419, 3,932,167, EP 191496, EP 273328, EP 411153/WO 90/09378). However, these compounds have hitherto not attained any particular importance.

DETAILED DESCRIPTION OF THE INVENTION

This invention now provides the novel substituted 2,4-diamino-1,3,5-triazines of the general formula (I)

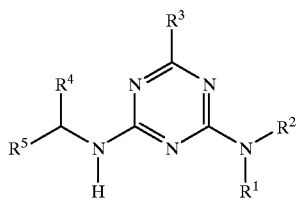

in which
- $R^1$ represents hydrogen or represents optionally cyano-, halogen- or $C_1$–$C_4$-alkoxy-substituted alkyl having 1 to 6 carbon atoms,
- $R^2$ represents hydrogen, represents optionally cyano-, halogen- or $C_1$–$C_4$-alkoxy-substituted alkyl having 1 to 6 carbon atoms or represents the grouping —CO—$R^6$,
- $R^3$ represents hydrogen, represents optionally cyano-, hydroxyl-, halogen-, $C_1$–$C_4$-alkoxy-, $C_1$–$C_4$-alkylthio-, $C_1$–$C_4$-alkylsulphinyl- or $C_1$–$C_4$-alkyl-sulphonyl-substituted alkyl having 1 to 6 carbon atoms, represents in each case optionally halogen- or $C_1$–$C_4$-alkoxy-substituted alkenyl or alkinyl having in each case 2 to 6 carbon atoms, or represents optionally cyano-, halogen- or $C_1$–$C_4$-alkyl-substituted cycloalkyl having 3 to 6 carbon atoms,
- $R^4$ represents hydrogen, represents optionally cyano-, halogen- or $C_1$–$C_4$-alkoxy-substituted alkyl having 1 to 6 carbon atoms, or represents optionally cyano-, halogen- or $C_1$–$C_4$-alkyl-substituted cycloalkyl having 3 to 6 carbon atoms,
- $R^5$ represents one of the groupings below,

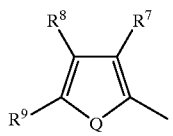 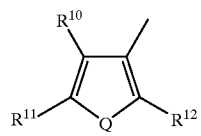

- $R^6$ represents hydrogen or represents in each case optionally cyano-, halogen- or $C_1$–$C_4$-alkoxy-substituted alkyl, alkoxy, alkylamino or dialkylamino having in each case 1 to 6 carbon atoms in the alkyl groups or represents optionally halogen-substituted alkenyl having 2 to 6 carbon atoms,
- $R^7$ represents hydrogen, nitro, cyano, carbamoyl, thiocarbamoyl, sulfamoyl, halogen, represents in each case optionally cyano-, halogen- or $C_1$–$C_4$-alkoxy-substituted alkyl, alkoxy, alkylthio, alkylsulphinyl, alkylsulphonyl, alkylcarbonyl, alkoxycarbonyl, alkylaminosulphonyl or dialkylaminosulphonyl having in each case 1 to 6 carbon atoms in the alkyl groups, represents optionally cyano-, halogen- or $C_1$–$C_4$-alkyl-substituted cycloalkyl, or represents in each case optionally nitro-, cyano-, carbamoyl-, thiocarbamoyl-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, phenoxy or phenylthio,
- $R^8$ represents hydrogen, nitro, cyano, carbamoyl, thiocarbamoyl, sulfamoyl, fluorine, bromine, represents cyano-, halogen- or $C_1$–$C_4$-alkoxy-substituted methyl, represents optionally cyano-, halogen- or $C_1$–$C_4$-alkoxy-substituted alkyl having 2 to 6 carbon atoms, represents in each case optionally cyano-, halogen- or $C_1$–$C_4$-alkoxy-substituted alkoxy, alkylthio, alkylsulphinyl, alkylsulphonyl, alkylcarbonyl, alkoxycarbonyl, alkylaminosulphonyl or dialkylaminosulphonyl having in each case 1 to 6 carbon atoms in the alkyl groups, represents optionally cyano-, halogen- or $C_1$–$C_4$-alkyl-substituted cycloalkyl, or represents in each case optionally nitro-, cyano-, carbamoyl-, thiocarbamoyl-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, phenoxy or phenylthio, and—if $R^9$ is different from chlorine or methyl—also represents chlorine or methyl,
- $R^9$ represents hydrogen, nitro, cyano, carbamoyl, thiocarbamoyl, sulfamoyl, fluorine, bromine, represents cyano-, halogen- or $C_1$–$C_4$-alkoxy-substituted methyl, represents optionally cyano-, halogen- or $C_1$–$C_4$-alkoxy-substituted alkyl having 2 to 6 carbon atoms, represents in each case optionally cyano-, halogen- or $C_1$–$C_4$-alkoxy-substituted alkoxy, alkylthio, alkylsulphinyl, alkylsulphonyl, alkylcarbonyl, alkoxycarbonyl, alkylaminosulphonyl or dialkylaminosulphonyl having in each case 1 to 6 carbon atoms in the alkyl groups, represents optionally cyano-, halogen- or $C_1$–$C_4$-alkyl-substituted cycloalkyl, or represents in each case optionally nitro-, cyano-, carbamoyl-, thiocarbamoyl-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, phenoxy or phenylthio, and—if $R^8$ is different from chlorine or methyl—also represents chlorine or methyl,
- $R^{10}$ represents hydrogen, nitro, cyano, carbamoyl, thiocarbamoyl, sulfamoyl, halogen, represents in each case optionally cyano-, halogen- or $C_1$–$C_4$-alkoxy-substituted alkyl, alkoxy, alkylthio, alkylsulphinyl, alkylsulphonyl, alkylcarbonyl, alkoxycarbonyl, alkylaminosulphonyl or dialkylaminosulphonyl having in each case 1 to 6 carbon atoms in the alkyl groups, represents optionally cyano-, halogen- or $C_1$–$C_4$-alkyl-substituted cycloalkyl, or represents in each case optionally nitro-, cyano-, carbamoyl-, thiocarbamoyl-, halogen-, $C_1$–$C_4$- alkyl-, $C_1$–$C_4$-halogenoalkyl-, $C_1$–$C_4$-alkoxy- or $C_1$–$C_4$-halogenoalkoxy-substituted phenyl, phenoxy or phenylthio, $R^{11}$ represents hydrogen, nitro, cyano, carbamoyl, thiocarbamoyl, sulfamoyl, halogen, represents in each case optionally cyano-, halogen- or $C_1$–$C_4$-alkoxy-substituted alkyl, alkoxy, alkylthio, alkylsulphinyl, alkylsulphonyl, alkylcarbonyl, alkoxycarbonyl, alkylaminosulphonyl or dialkylaminosulphonyl having in each case 1 to 6 carbon atoms in the alkyl groups, represents optionally cyano-, halogen- or $C_1$–$C_4$-alkyl-substituted cycloalkyl, or represents in each case optionally nitro-, cyano-, carbamoyl-, thiocarbamoyl-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, phenoxy or phenylthio, $R^{12}$ represents hydrogen, nitro, cyano, carbamoyl, thiocarbamoyl, sulfamoyl, halogen, represents in each case optionally cyano-, halogen- or $C_1$–$C_4$-alkoxy-substituted alkyl, alkoxy, alkylthio, alkylsulphinyl, alkylsulphonyl, alkylcarbonyl, alkoxycarbonyl, alkylaminosulphonyl or dialkylaminosulphonyl having in each case 1 to 6 carbon atoms in the alkyl groups, represents optionally cyano-, halogen- or $C_1$–$C_4$-alkyl-substituted cycloalkyl, or represents in each case optionally nitro-, cyano-, carbamoyl-, thiocarbamoyl-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, phenoxy or phenylthio, and Q represents oxygen or sulphur.

The novel substituted 2,4-diamino-1,3,5-triazines of the general formula (I) are obtained when (a) substituted biguanides of the general formula (I)

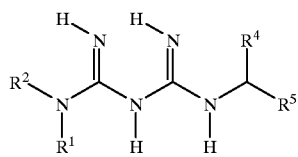

(II)

in which
$R^1$, $R^2$, $R^4$ and $R^5$ are as defined above,—and/or acid adducts of compounds of the general formula (II)—are reacted with alkoxycarbonyl compounds of the general formula (III)

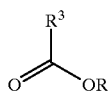

(III)

in which
$R^3$ is as defined above and
R represents alkyl, if appropriate in the presence of a reaction auxiliary and if appropriate in the presence of a diluent, or when (b) to prepare compounds of the formula (I) in which $R^2$ is different from hydrogen, 2,4-diamino-1,3,5-triazines of the general formula (Ia)

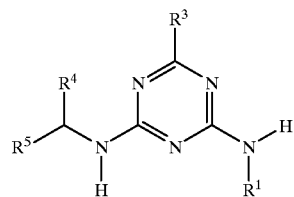

(Ia)

in which
$R^1$, $R^3$, $R^4$ and $R^5$ are as defined above are reacted with alkylating or acylating agents of the general formula (IV)

$$X-R^2 \quad (IV)$$

in which
$R^2$ is as defined above, except for hydrogen, and
X represents halogen, alkoxy, —O—CO—$R^6$ or —O—SO$_2$—O—$R^2$, if appropriate in the presence of a reaction auxiliary and if appropriate in the presence of a diluent, and if appropriate further conversions within the scope of the above definition of substituents are carried out by customary methods on the compounds of the general formula (I) obtained by the processes described under (a) or (b).

The novel substituted 2,4-diamino-1,3,5-triazines of the general formula (I) have strong and selective herbicidal activity.

To a certain extent, the compounds of the general formula (I) also have fungicidal and insecticidal activity.

If appropriate, the compounds of the general formula (I) according to the invention contain an asymmetrically substituted carbon atom, in which case they can be present in different enantiomeric (R- and S-configured forms) and/or diastereomeric forms. The invention relates both to the various possible individual enantiomeric or stereo-isomeric forms of the compounds of the general formula (I) and to the mixtures of these isomeric compounds.

In the definitions, the hydrocarbon chains, such as alkyl—including combination with heteroatoms, such as in alkoxy or alkylthio—are in each case straight-chain or branched.

Halogen generally represents fluorine, chlorine, bromine or iodine, preferably fluorine, chlorine or bromine, in particular fluorine or chlorine.

The invention preferably provides compounds of the formula (I) in which $R^1$ represents hydrogen or represents in each case optionally cyano-, fluorine-, chlorine-, methoxy- or ethoxy-substituted methyl, ethyl, n- or i-propyl, n-, i-, s- or t-butyl, $R^2$ represents hydrogen, represents in each case optionally cyano-, fluorine-, chlorine-, methoxy- or ethoxy-substituted methyl, ethyl, n- or i-propyl, n-, i-, s- or t-butyl or represents the grouping —CO—$R^6$, $R^3$ represents hydrogen, represents in each case optionally cyano-, hydroxyl-, fluorine-, chlorine-, bromine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl-, ethylsulphonyl-, n- or i-propylsulphonyl-substituted methyl, ethyl, n- or i-propyl, n-, i-, s- or t-butyl, represents in each case optionally fluorine-, chlorine-, bromine-, methoxy- or ethoxy-substituted ethenyl, propenyl, butenyl, ethinyl, propinyl or butinyl, or represents in each case optionally cyano-, fluorine-, chlorine-, bromine-, methyl- or ethyl-substituted cyclopropyl, cyclobutyl, cyclopentyl or cyclohexyl, $R^4$ represents hydrogen, represents in each case optionally cyano-, fluorine-, chlorine-, methoxy- or ethoxy-substituted methyl, ethyl, n- or i-propyl, n-, i-, s- or t-butyl, or represents in each case optionally cyano-, fluorine-, chlorine-, methyl- or ethyl-substituted cyclopropyl, cyclobutyl, cyclopentyl or cyclohexyl, $R^5$ represents one of the groupings below,

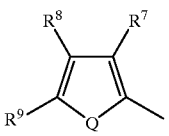 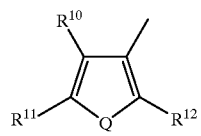

$R^6$ represents hydrogen or represents in each case optionally cyano-, fluorine-, chlorine-, bromine-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, methylamino, ethylamino, n- or i-propylamino, n-, i-, s- or t-butylamino, dimethylamino or diethylamino, or represents in each case optionally fluorine-, chlorine-, and/or bromine-substituted ethenyl, propenyl or butenyl, $R^7$ represents hydrogen, nitro, cyano, carbamoyl, thiocarbamoyl, sulfamoyl, fluorine, chlorine, bromine, represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl, ethylsulphonyl, acetyl, propionyl, n- or i-butyroyl, methoxycarbonyl, ethoxycarbonyl, methylaminosulphonyl, ethylaminosulphonyl, dimethylaminosulphonyl or diethylaminosulphonyl, represents in each case optionally cyano-, fluorine-, chlorine-, bromine-, methyl- or ethyl-substituted cyclopropyl, cyclobutyl, cyclopentyl or cyclohexyl, or represents in each case optionally nitro-, cyano-, carbamoyl-, thiocarbamoyl-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted phenyl, phenoxy or phenylthio, $R^8$ represents hydrogen, nitro, cyano, carbamoyl, thiocarbamoyl, sulfamoyl, fluorine, bromine, represents cyano-, fluorine-, chlorine-, bromine-, methoxy- or ethoxy-substituted methyl, represents in each case optionally cyano-, fluorine-, chlorine-, methoxy- or ethoxy-substituted ethyl, n- or i-propyl, n-, i-, s- or t-butyl, represents in each case optionally cyano-, fluorine-, chlorine-, methoxy- or ethoxy-substituted methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl, ethylsulphonyl, acetyl, propionyl, n- or i-butyroyl, methoxycarbonyl, ethoxycarbonyl, methylaminosulphonyl, ethylaminosulphonyl, dimethylaminosulphonyl or diethylaminosulphonyl, represents in each case optionally cyano-, fluorine-, chlorine-, bromine-, methyl- or ethyl-substituted cyclopropyl, cyclobutyl, cyclopentyl or cyclohexyl, or represents in each case optionally nitro-, cyano-, carbamoyl-, thiocarbamoyl-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted phenyl, phenoxy or phenylthio, and—if $R^9$ is different from chlorine or methyl—also represents chlorine or methyl.

$R^9$ represents hydrogen, nitro, cyano, carbamoyl, thiocarbamoyl, sulfamoyl, fluorine, bromine, represents cyano-, fluorine-, chlorine-, methoxy- or ethoxy-substituted methyl, represents in each case optionally cyano-, fluorine-, chlorine-, methoxy- or ethoxy-substituted ethyl, n- or i-propyl, n-, i-, s- or t-butyl, represents in each case optionally cyano-, fluorine-, chlorine-, bromine-, methoxy- or ethoxy-substituted methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl, ethylsulphonyl, acetyl, propionyl, n- or i-butyroyl, methoxycarbonyl, ethoxycarbonyl, methylaminosulphonyl, ethylaminosulphonyl, dimethylaminosulphonyl or diethylaminosulphonyl, represents in each case optionally cyano-, fluorine-, chlorine-, bromine-, methyl- or ethyl-substituted cyclopropyl, cyclobutyl, cyclopentyl or cyclohexyl, or represents in each case optionally nitro-, cyano-, carbamoyl-, thiocarbamoyl-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted phenyl, phenoxy or phenylthio, and—if $R^8$ is different from chlorine or methyl—also represents chlorine or methyl.

$R^{10}$ represents hydrogen, nitro, cyano, carbamoyl, thiocarbamoyl, sulphamoyl, fluorine, chlorine, bromine, represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl, ethylsulphonyl, acetyl, propionyl, n- or i-butyroyl, methoxycarbonyl, ethoxycarbonyl, methylaminosulphonyl, ethylaminosulphonyl, dimethylaminosulphonyl or diethylaminosulphonyl, represents in each case optionally cyano-, fluorine-, chlorine-, bromine-, methyl- or ethyl-substituted cyclopropyl, cyclobutyl, cyclopentyl or cyclohexyl, or represents in each case optionally nitro-, cyano-, carbamoyl-, thiocarbamoyl-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoro-methoxy-substituted phenyl, phenoxy or phenylthio, $R^{11}$ represents hydrogen, nitro, cyano, carbamoyl, thiocarbamoyl, sulphamoyl, fluorine, chlorine, bromine, represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl, ethylsulphonyl, acetyl, propionyl, n- or i-butyroyl, methoxycarbonyl, ethoxycarbonyl, methylaminosulphonyl, ethylaminosulphonyl, dimethylaminosulphonyl or diethylaminosulphonyl, represents in each case optionally cyano-, fluorine-, chlorine-, bromine-, methyl- or ethyl-substituted cyclopropyl, cyclobutyl, cyclopentyl or cyclohexyl, or represents in each case optionally nitro-, cyano-, carbamoyl-, thiocarbamoyl-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoro-methoxy-substituted phenyl, phenoxy or phenylthio, $R^{12}$ represents hydrogen, nitro, cyano, carbamoyl, thiocarbamoyl, sulphamoyl, fluorine, chlorine, bromine, represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl, ethylsulphonyl, acetyl, propionyl, n- or i-butyroyl, methoxycarbonyl, ethoxycarbonyl, methylaminosulphonyl, ethylaminosulphonyl, dimethylaminosulphonyl or diethylaminosulphonyl, represents in each case optionally cyano-, fluorine-, chlorine-, bromine-, methyl- or ethyl-substituted cyclopropyl, cyclobutyl, cyclopentyl or cyclohexyl, or represents in each case optionally nitro-, cyano-, carbamoyl-, thiocarbamoyl-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoro-methoxy-substituted phenyl, phenoxy or phenylthio, and Q represents oxygen or sulphur.

The invention relates in particular to compounds of the formula (I) in which $R^1$ represents hydrogen, $R^2$ represents hydrogen or represents the grouping —CO—$R^6$, $R^3$ represents hydrogen, represents in each case optionally cyano-, hydroxyl-, fluorine-, chlorine-, methoxy-, ethoxy-, methylthio-, ethylthio-, methylsulphinyl-, ethylsulphinyl-, methylsulphonyl- or ethylsulphonyl-substituted methyl, ethyl, n- or i-propyl, represents in each case optionally fluorine-, chlorine- or methoxy-substituted ethenyl or propenyl, or represents in each case optionally cyano-, fluorine-, chlorine- or methyl-substituted cyclopropyl, $R^4$ represents in each case optionally cyano-, fluorine-, chlorine-, methoxy- or ethoxy-substituted methyl, ethyl, n- or i-propyl, or represents optionally cyano-, fluorine-, chlorine- or methyl-substituted cyclopropyl, $R^5$ represents one of the groupings below,

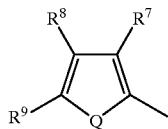 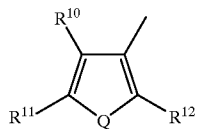

$R^6$ represents hydrogen or represents in each case optionally cyano-, fluorine-, chlorine-, methoxy- or ethoxy-substituted methyl, ethyl, n- or i-propyl, methoxy or ethoxy, or represents in each case optionally fluorine- and/or chlorine-substituted ethenyl or propenyl, $R^7$ represents hydrogen, nitro, cyano, carbamoyl, thiocarbamoyl, sulphamoyl, fluorine, chlorine, bromine, represents in each case optionally cyano-, fluorine-, chlorine-, methoxy- or ethoxy-substituted methyl, ethyl, n- or i-propyl, methoxy, ethoxy, n- or i-propoxy, methylthio, ethylthio, n- or i-propylthio, methylsulphinyl, ethylsulphinyl, methylsulphonyl, ethylsulphonyl, acetyl, propionyl, methoxycarbonyl, ethoxycarbonyl, represents optionally cyano-, fluorine-, chlorine- or methyl-substituted cyclopropyl, or represents in each case optionally nitro-, cyano-, carbamoyl-, thiocarbamoyl-, fluorine-, chlorine-, bromine-, methyl-, trifluoromethyl-, methoxy-, difluoromethoxy- or trifluoro-methoxy-substituted phenyl, phenoxy or phenylthio, $R^8$ represents hydrogen, nitro, cyano, carbamoyl, thiocarbamoyl, sulphamoyl, fluorine, bromine, represents in each case optionally cyano-, fluorine-, chlorine-, methoxy- or ethoxy-substituted ethyl, n- or i-propyl, represents in each case optionally cyano-, fluorine-, chlorine-, methoxy- or ethoxy-substituted methoxy, ethoxy, n- or i-propoxy, methylthio, ethylthio, n- or i-propylthio, methylsulphinyl, ethylsulphinyl, methylsulphonyl, ethylsulphonyl, acetyl, propionyl, methoxycarbonyl, ethoxycarbonyl, represents optionally cyano-, fluorine-, chlorine- or methyl-substituted cyclopropyl, or represents in each case optionally nitro-, cyano-, carbamoyl-, thiocarbamoyl-, fluorine-, chlorine-, bromine-, methyl-, trifluoromethyl-, methoxy-, difluoromethoxy- or trifluoromethoxy-substituted phenyl, phenoxy or phenylthio, and—if $R^9$ is different from chlorine or methyl—also represents chlorine or methyl, $R^9$ represents hydrogen, nitro, cyano, carbamoyl, thiocarbamoyl, sulphamoyl, fluorine, bromine, represents in each case optionally cyano-, fluorine-, chlorine-, methoxy- or ethoxy-substituted ethyl, n- or i-propyl, represents in each case optionally cyano-, fluorine-, chlorine-, bromine-, methoxy- or ethoxy-substituted methoxy, ethoxy, n- or i-propoxy, methylthio, ethylthio, n- or i-propylthio, methylsulphinyl, ethylsulphinyl, methylsulphonyl, ethylsulphonyl, acetyl, propionyl, methoxycarbonyl, ethoxycarbonyl, represents optionally cyano-, fluorine-, chlorine- or methyl-substituted cyclopropyl, or represents in each case optionally nitro-, cyano-, carbamoyl-, thiocarbamoyl-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted phenyl, phenoxy or phenylthio, and—if $R^8$ is different from chlorine or methyl—also represents chlorine or methyl, $R^{10}$ represents hydrogen, nitro, cyano, carbamoyl, thiocarbamoyl, sulphamoyl, fluorine, chlorine, bromine, represents in each case optionally cyano-, fluorine-, chlorine-, methoxy- or ethoxy-substituted methyl, ethyl, n- or i-propyl, methoxy, ethoxy, n- or i-propoxy, methylthio, ethylthio, n- or i-propylthio, methylsulphinyl, ethylsulphinyl, methylsulphonyl, ethylsulphonyl, acetyl, propionyl, methoxycarbonyl, ethoxycarbonyl, represents optionally cyano-, fluorine-, chlorine- or methyl-substituted cyclopropyl, or represents in each case optionally nitro-, cyano-, carbamoyl-, thiocarbamoyl-, fluorine-, chlorine-, bromine-, methyl-, trifluoromethyl-, methoxy-, difluoromethoxy- or trifluoro-methoxy-substituted phenyl, phenoxy or phenylthio, $R^{11}$ represents hydrogen, nitro, cyano, carbamoyl, thiocarbamoyl, sulphamoyl, fluorine, chlorine, bromine, represents in each case optionally cyano-, fluorine-, chlorine-, methoxy- or ethoxy-substituted methyl, ethyl, n- or i-propyl, methoxy, ethoxy, n- or i-propoxy, methylthio, ethylthio, n- or i-propylthio, methylsulphinyl, ethylsulphinyl, methylsulphonyl, ethylsulphonyl, acetyl, propionyl, methoxycarbonyl, ethoxycarbonyl, represents optionally cyano-, fluorine-, chlorine- or methyl-substituted cyclopropyl, or represents in each case optionally nitro-, cyano-, carbamoyl-, thiocarbamoyl-, fluorine-, chlorine-, bromine-, methyl-, trifluoromethyl-, methoxy-, difluoromethoxy- or trifluoro-methoxy-substituted phenyl, phenoxy or phenylthio, $R^{12}$ represents hydrogen, nitro, cyano, carbamoyl, thiocarbamoyl, sulphamoyl, fluorine, chlorine, bromine, represents in each case optionally cyano-, fluorine-, chlorine-, methoxy- or ethoxy-substituted methyl, ethyl, n- or i-propyl, methoxy, ethoxy, n- or i-propoxy, methylthio, ethylthio, n- or i-propylthio, methylsulphinyl, ethylsulphinyl, methylsulphonyl, ethylsulphonyl, acetyl, propionyl, methoxycarbonyl, ethoxycarbonyl, represents optionally cyano-, fluorine-, chlorine- or methyl-substituted cyclopropyl, or represents in each case optionally nitro-, cyano-, carbamoyl-, thiocarbamoyl-, fluorine-, chlorine-, bromine-, methyl-, trifluoromethyl-, methoxy-, difluoromethoxy- or trifluoro-methoxy-substituted phenyl, phenoxy or phenylthio, and Q represents oxygen or sulphur.

The general or preferred radical definitions listed above apply both to the end products of the formula (I) and correspondingly to the starting materials or intermediates required in each case for the preparation. These radical definitions can be combined with one another in any way, i.e. including combinations between the given preferred ranges.

Examples of the compounds of the formula (I) according to the invention are listed in the groups below. Here, the general formulae in each case represent the R enantiomers, the S enantiomers and the racemates.

Group 1

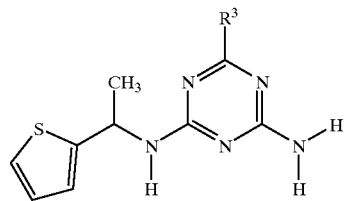

(I-1)

Here, $R^3$ has, for example, the meanings given below: hydrogen, methyl, ethyl, n- or i-propyl, n-, i-, s- or t-butyl, cyanomethyl, 1-cyano-ethyl, 2-cyano-ethyl, 1-cyano-1-methyl-ethyl, hydroxymethyl, 1-hydroxy-ethyl, 2-hydroxy-ethyl, fluoromethyl, difluoromethyl, trifluoromethyl, chloromethyl, dichloromethyl, chlorofluoromethyl, chlorobromomethyl, chlorodifluoromethyl, fluorodichloromethyl, bromodifluoromethyl, trichloromethyl, 1-fluoro-ethyl, 2-fluoro-ethyl, 1-chloro-ethyl, 2-chloro-ethyl, 1-chloro-1-fluoro-ethyl, 1-fluoro-propyl, 2-fluoro-propyl, 3-fluoro-propyl, 1-fluoro-1-methyl-ethyl, 2-fluoro-1-methyl-ethyl, 1-chloro-1-methyl-ethyl, 1-fluoro-1-methyl-propyl, 1-chloro-1-ethyl-propyl, 1-fluoro-1-ethyl-propyl, 1-chloro-1-ethyl-propyl, 1-fluoro-2-methyl-propyl, 1-chloro-2-methyl-propyl, 1-chloro-propyl, 2-chloro-propyl, 3-chloro-propyl, 1-chloro-1-methyl-ethyl, 2-chloro-1-methyl-ethyl, 1,1-difluoro-ethyl, 1,2-difluoro-ethyl, 1,1-dichloro-ethyl, 2,2,2-trifluro-ethyl, 1,2,2,2-tetrafluoro-ethyl, perfluoroethyl, 1,1-difluoro-propyl, 1,1-dichloro-propyl, perfluoropropyl, 1-fluoro-butyl, 1-chloro-butyl, perfluoropentyl, perfluorohexyl, methoxymethyl, 1,1-dimethoxy-methyl, 1-methoxyethyl, 2-methoxy-ethyl, 1,1-dimethoxy-ethyl, ethoxymethyl, 1-ethoxyethyl, 2-ethoxy-ethyl, 2-methoxy-1-methyl-ethyl, 2-methoxy-1-ethyl-ethyl, 2-ethoxy-1-methyl-ethyl, 2-ethoxy-1-ethyl-ethyl, methylthiomethyl, ethylthiomethyl, 1-methylthio-ethyl, 2-methylthioethyl, 1-ethylthio-ethyl, 2-ethylthioethyl, methylsulphinyl-methyl, ethylsulphinylmethyl, methylsulphonylmethyl, ethylsulphonylmethyl, vinyl, 1-chloro-vinyl, 2-chloro-vinyl, 1-fluoro-vinyl, 2-fluoro-vinyl, 1-bromo-vinyl, 2-bromo-vinyl, 1,2-dichloro-vinyl, 1,2-dibromo-vinyl, 1,2-difluoro-vinyl, 2,2-dichloro-vinyl, 2,2-difluoro-vinyl, 2,2-dibromo-vinyl, 1-chloro-2-fluoro-vinyl, 2-bromo-2-chloro-vinyl, trichlorovinyl, allyl, 2-chloro-allyl, 3-chloro-allyl, 3,3-dichloro-allyl, 1-propenyl, isopropenyl, 1-chloro-2-propenyl, 1-fluoro-2-propenyl, 1-bromo-2-propenyl, 1,2-dichloro-1-propenyl, 1,2-dibromo-1-propenyl, 1,2-difluoro-1-propenyl, 1,1-dichloro-2-propenyl, 1,1-dibromo-2-propenyl, 1,1-difluoro-2-propenyl, 1,1,3,3,3-pentafluoro-2-propenyl, 2-buten-1-yl, 2-buten-2-yl, 3-chloro-2-butenyl, 3-bromo-2-butenyl, 3,3,3-trifluoro-2-butenyl, ethinyl, 2-chloro-ethinyl, 2-bromo-ethinyl, 1-propinyl, 2-propinyl, 3,3,3-trifluoro-1-propinyl, cyclopropyl, 2-fluoro-cyclopropyl, 2-chloro-cyclopropyl, 2,2-difluoro-cyclopropyl, 2,2-dichloro-cyclopropyl.

Group 2

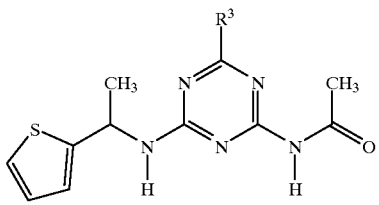

(I-2)

Here, $R^3$ has, for example, the meanings given above in group 1.

Group 3

(I-3)

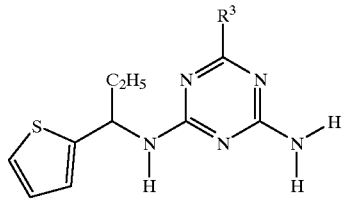

Here, R³ has, for example, the meanings given above in group 1.

Group 4

(I-4)

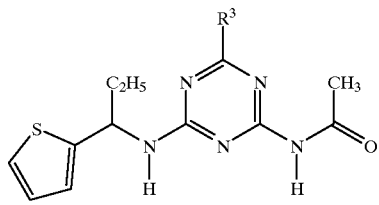

Here, R³ has, for example, the meanings given above in group 1.

Group 5

(I-5)

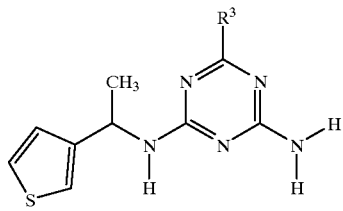

Here, R³ has, for example, the meanings given above in group 1.

Group 6

(I-6)

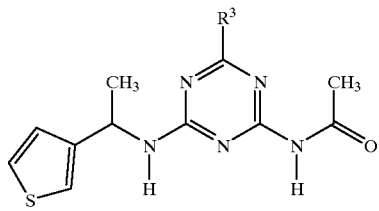

Here, R³ has, for example, the meanings given above in group 1.

Group 7

(I-7)

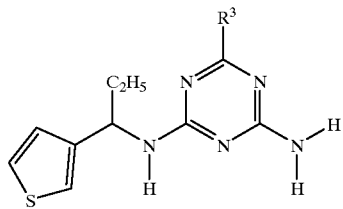

Here, R³ has, for example, the meanings given above in group 1.

Group 8

(I-8)

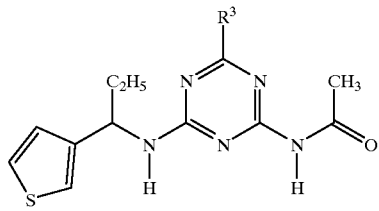

Here, R³ has, for example, the meanings given above in group 1.

Group 9

(I-9)

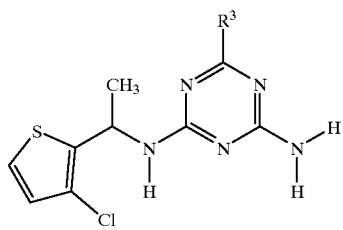

Here, R³ has, for example, the meanings given above in group 1.

Group 10

(I-10)

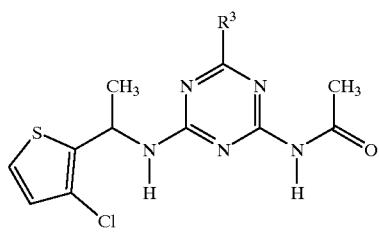

Here, R³ has, for example, the meanings given above in group 1.

Group 11

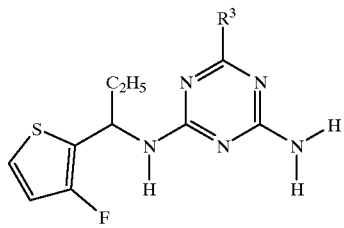
(I-11)

Here, R³ has, for example, the meanings given above in group 1.

Group 12

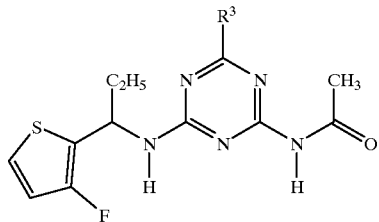
(I-12)

Here, R³ has, for example, the meanings given above in group 1.

Group 13

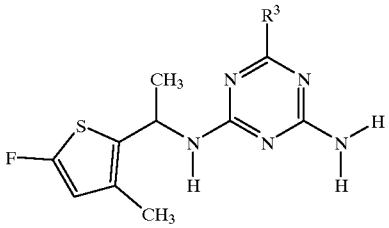
(I-13)

Here, R³ has, for example, the meanings given above in group 1.

Group 14

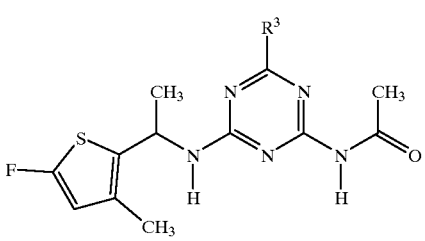
(I-14)

Here, R³ has, for example, the meanings given above in group 1.

Group 15

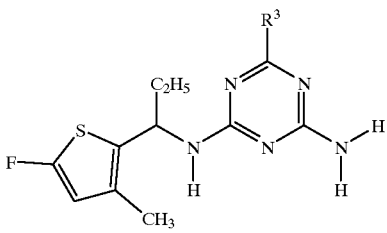
(I-15)

Here, R³ has, for example, the meanings given above in group 1.

Group 16

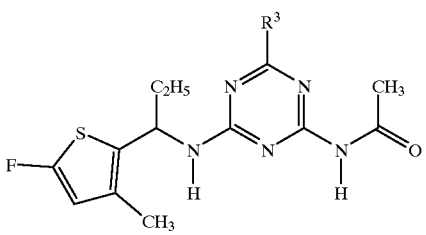
(I-16)

Here, R³ has, for example, the meanings given above in group 1.

Group 17

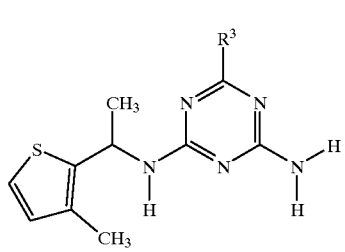
(I-17)

Here, R³ has, for example, the meanings given above in group 1.

Group 18

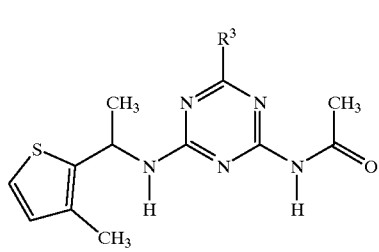
(I-18)

Here, R³ has, for example, the meanings given above in group 1.

Group 19

(I-19)

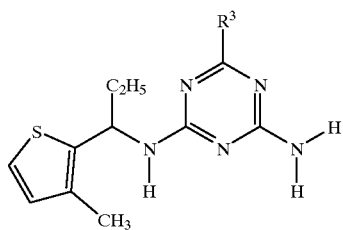

Here, R³ has, for example, the meanings given above in group 1.

Group 20

(I-20)

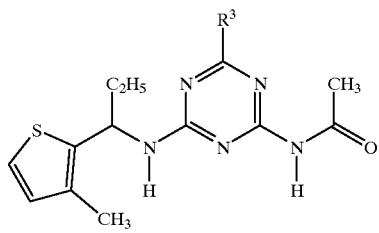

Here, R³ has, for example, the meanings given above in group 1.

Group 21

(I-21)

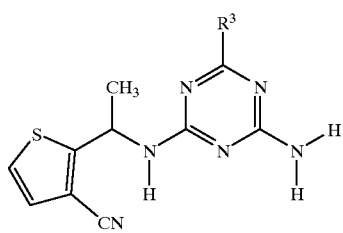

Here, R³ has, for example, the meanings given above in group 1.

Group 22

(I-22)

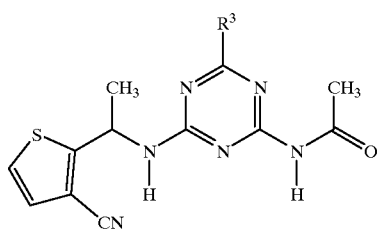

Here, R³ has, for example, the meanings given above in group 1.

Group 23

(I-23)

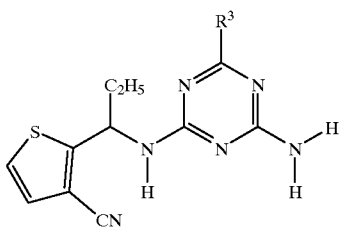

Here, R³ has, for example, the meanings given above in group 1.

Group 24

(I-24)

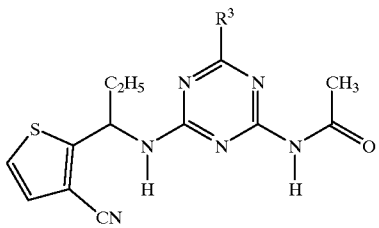

Here, R³ has, for example, the meanings given above in group 1.

Group 25

(I-25)

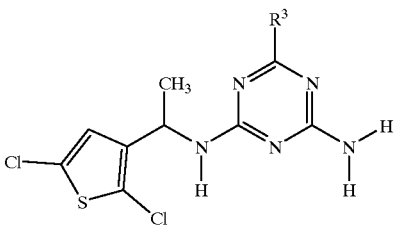

Here, R³ has, for example, the meanings given above in group 1.

Group 26

(I-26)

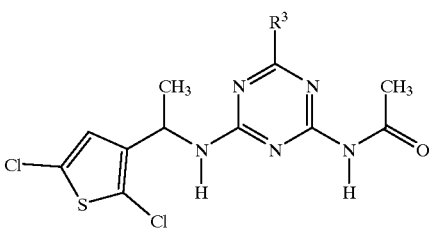

Here, R³ has, for example, the meanings given above in group 1.

Group 27

(I-27)

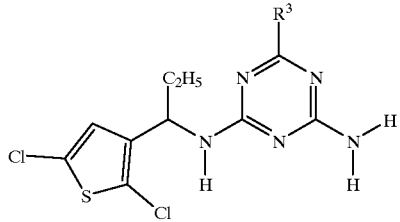

Here, R³ has, for example, the meanings given above in group 1.

Group 28

(I-28)

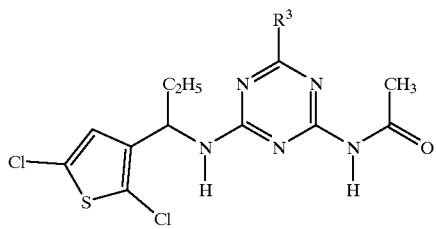

Here, R³ has, for example, the meanings given above in group 1.

Group 29

(I-29)

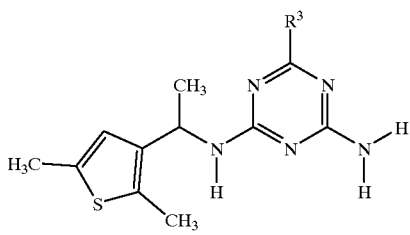

Here, R³ has, for example, the meanings given above in group 1.

Group 30

(I-30)

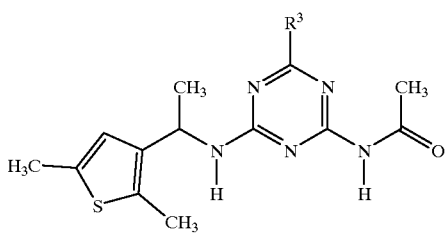

Here, R³ has, for example, the meanings given above in group 1.

Group 31

(I-31)

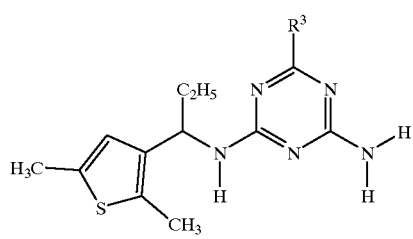

Here, R³ has, for example, the meanings given above in group 1.

Group 32

(I-32)

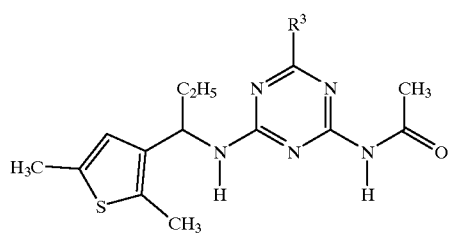

Here, R³ has, for example, the meanings given above in group 1.

Group 33

(I-33)

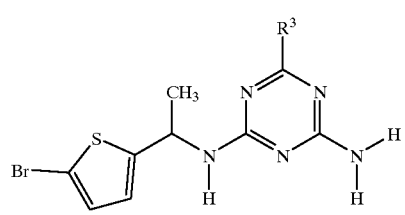

Here, R³ has, for example, the meanings given above in group 1.

Group 34

(I-34)

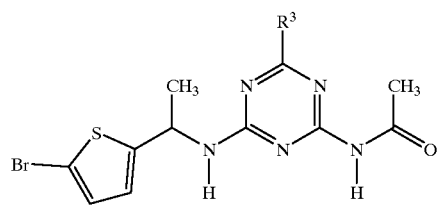

Here, R³ has, for example, the meanings given above in group 1.

Group 35

(I-35)

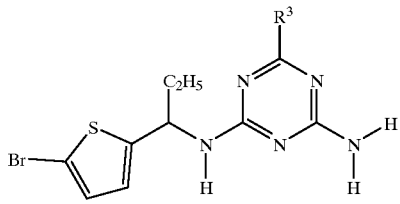

Here, R³ has, for example, the meanings given above in group 1.

Group 36

(I-36)

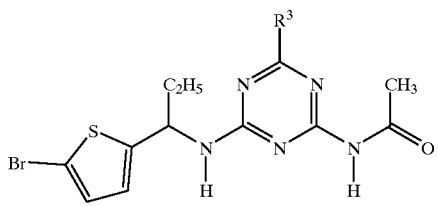

Here, R³ has, for example, the meanings given above in group 1.

Group 37

(I-37)

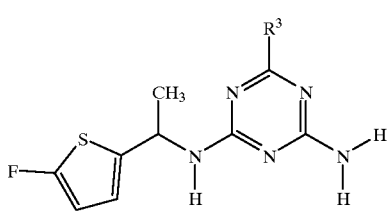

Here, R³ has, for example, the meanings given above in group 1.

Group 38

(I-38)

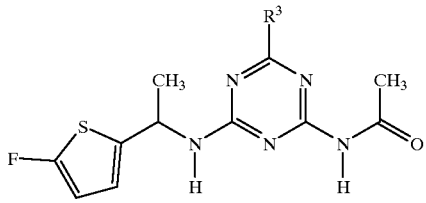

Here, R³ has, for example, the meanings given above in group 1.

Group 39

(I-39)

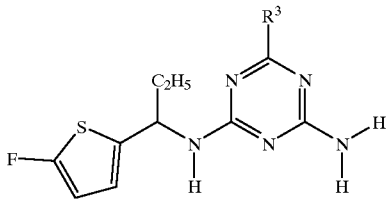

Here, R³ has, for example, the meanings given above in group 1.

Group 40

(I-40)

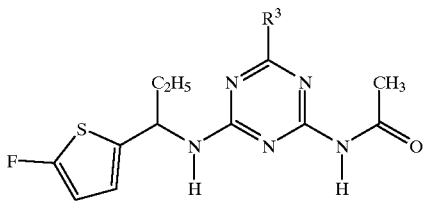

Here, R³ has, for example, the meanings given above in group 1.

Group 41

(I-41)

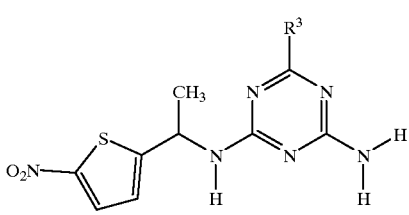

Here, R³ has, for example, the meanings given above in group 1.

Group 42

(I-42)

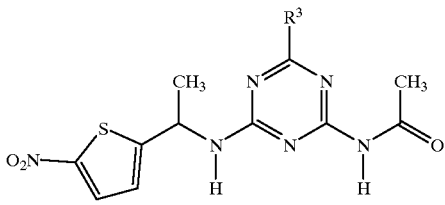

Here, R³ has, for example, the meanings given above in group 1.

Group 43

(I-43)

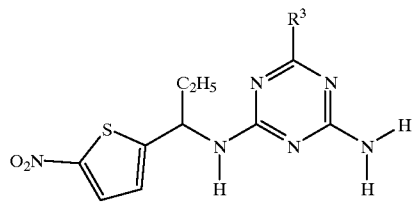

Here, R³ has, for example, the meanings given above in group 1.

Group 44

(I-44)

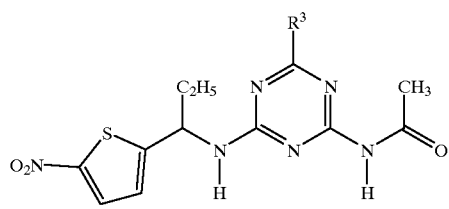

Here, R³ has, for example, the meanings given above in group 1.

Group 45

(I-45)

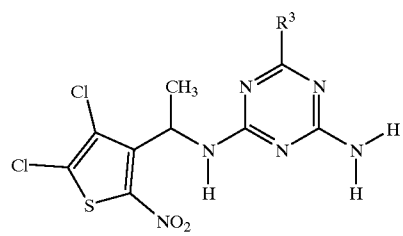

Here, R³ has, for example, the meanings given above in group 1.

Group 46

(I-46)

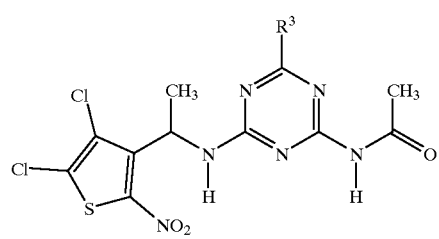

Here, R³ has, for example, the meanings given above in group 1.

Group 47

(I-47)

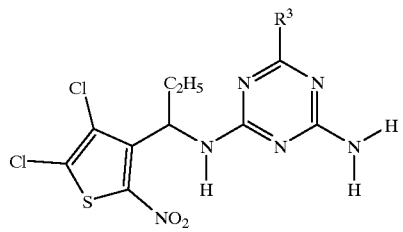

Here, R³ has, for example, the meanings given above in group 1.

Group 48

(I-48)

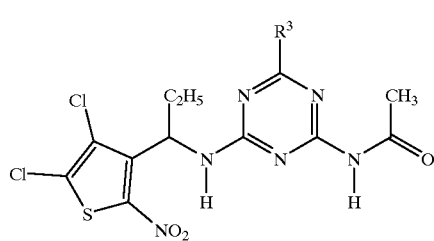

Here, R³ has, for example, the meanings given above in group 1.

Group 49

(I-49)

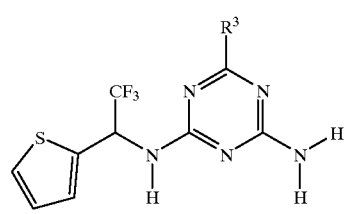

Here R³ as, for example, the meanings given above in group 1.

Group 50

(I-50)

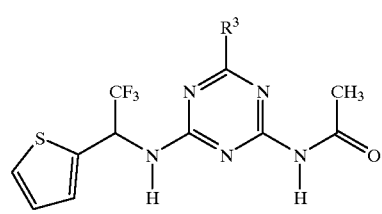

Here, R³ has, for example, the meanings given above in group 1.

Group 51

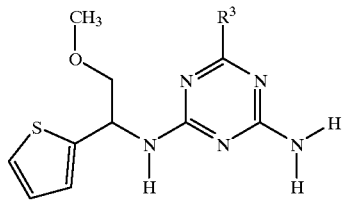
(I-51)

Here, R³ has, for example, the meanings given above in group 1.

Group 52

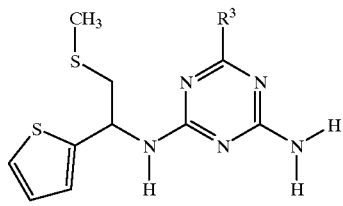
(I-52)

Here, R³ has, for example, the meanings given above in group 1.

Group 53

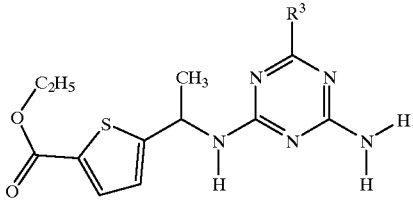
(I-53)

Here, R³ has, for example, the meanings given above in group 1.

Group 54

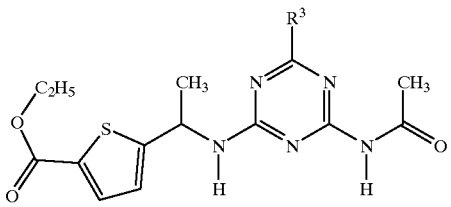
(I-54)

Here, R³ has, for example, the meanings given above in group 1.

Group 55

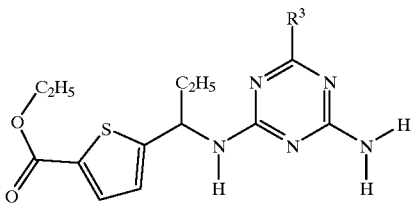
(I-55)

Here, R³ has, for example, the meanings given above in group 1.

Group 56

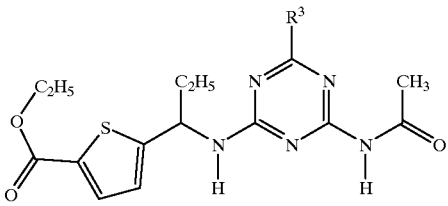
(I-56)

Here, R³ has, for example, the meanings given above in group 1.

Group 57

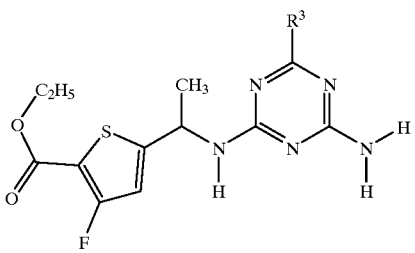
(I-57)

Here, R³ has, for example, the meanings given above in group 1.

Group 58

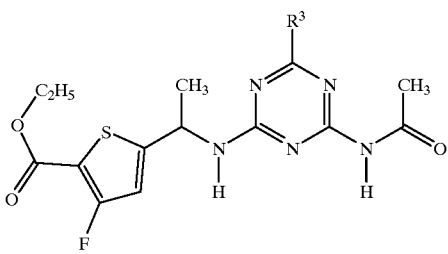
(I-58)

Here, R³ has, for example, the meanings given above in group 1.

Group 59

(I-59)

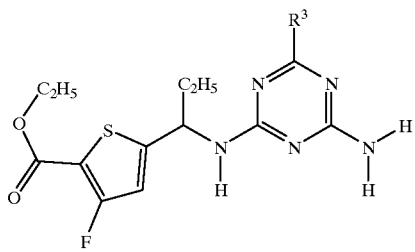

Here, R³ has, for example, the meanings given above in group 1.

Group 60

(I-60)

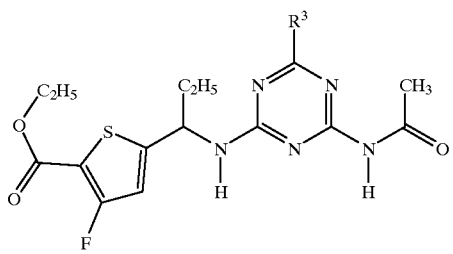

Here, R³ has, for example, the meanings given above in group 1.

Group 61

(I-61)

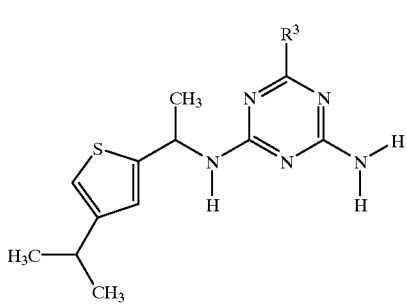

Here, R³ has, for example, the meanings given above in group 1.

Group 62

(I-62)

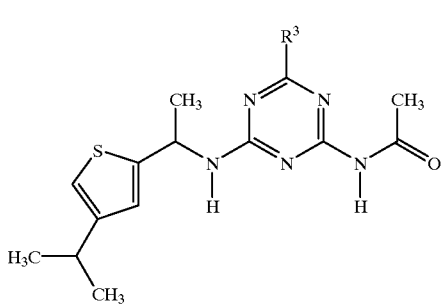

Here, R³ has, for example, the meanings given above in group 1.

Group 63

(I-63)

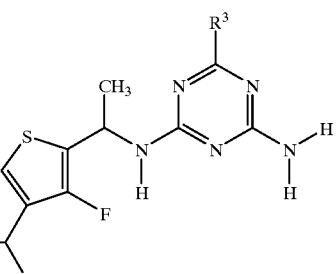

Here, R³ has, for example, the meanings given above in group 1.

Group 64

(I-64)

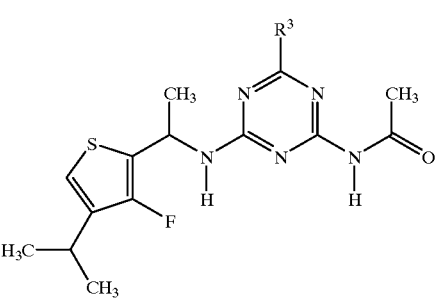

Here, R³ has, for example, the meanings given above in group 1.

Group 65

(I-65)

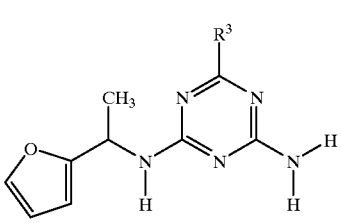

Here, R³ has, for example, the meanings given above in group 1.

Group 66

(I-66)

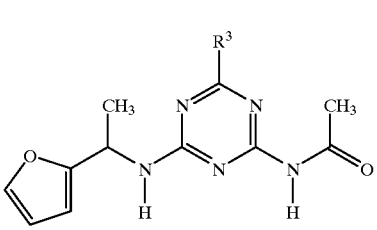

Group 67

(I-67)

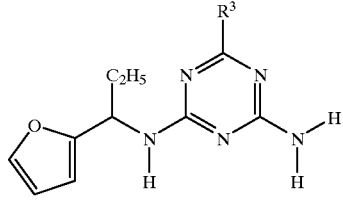

Here, R³ has, for example, the meanings given above in group 1.

Group 68

(I-68)

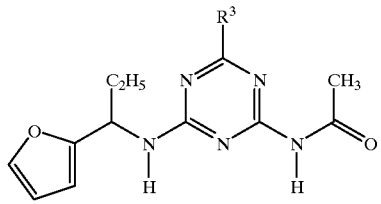

Here, R³ has, for example, the meanings given above in group 1.

Group 69

(I-69)

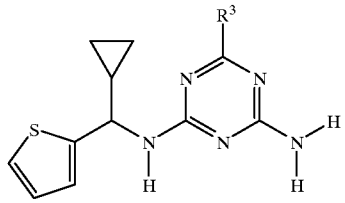

Here, R³ has, for example, the meanings given above in group 1.

Group 70

(I-70)

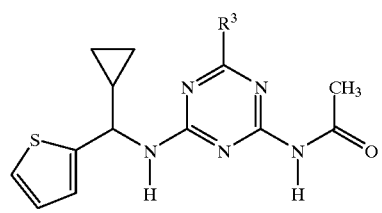

Here, R³ has, for example, the meanings given above in group 1.

Group 71

(I-71)

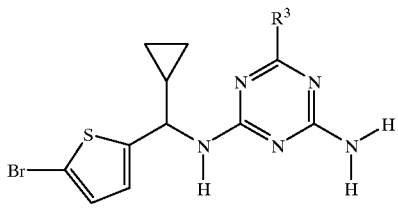

Here, R³ has, for example, the meanings given above in group 1.

Group 72

(I-72)

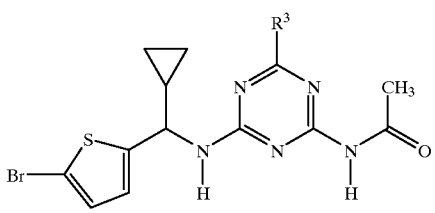

Here, R³ has, for example, the meanings given above in group 1.

Group 73

(I-73)

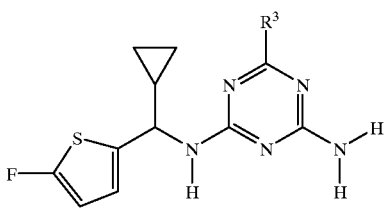

Here, R³ has, for example, the meanings given above in group 1.

Group 74

(I-74)

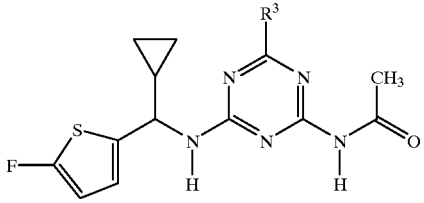

Here, R³ has, for example, the meanings given above in group 1.

Group 75

(I-75)

Here, R³ has, for example, the meanings given above in group 1.

Group 76

(I-76)

Here, R³ has, for example, the meanings given above in group 1.

Group 77

(I-77)

Here, R³ has, for example, the meanings given above in group 1.

Group 78

(I-78)

Here, R³ has, for example, the meanings given above in group 1.

Group 79

(I-79)

Here, R³ has, for example, the meanings given above in group 1.

Group 80

(I-80)

Here, R³ has, for example, the meanings given above in group 1.

Group 81

(I-81)

Here, R³ has, for example, the meanings given above in group 1.

Group 82

(I-82)

Here, R³ has, for example, the meanings given above in group 1.

Group 83

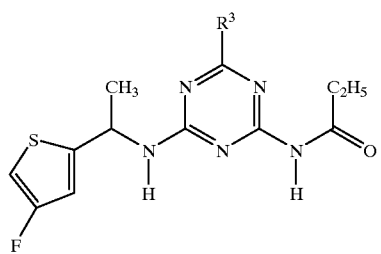
(I-83)

Here, R³ has, for example, the meanings given above in group 1.

Group 84

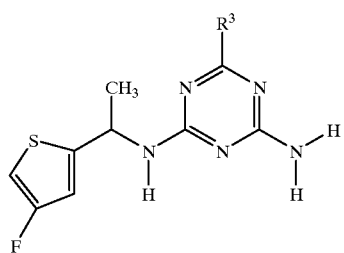
(I-84)

Here, R³ has, for example, the meanings given above in group 1.

Group 85

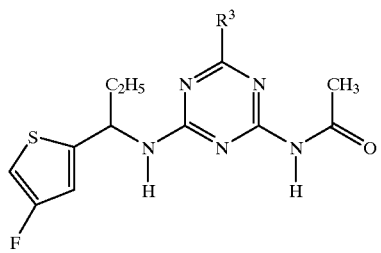
(I-85)

Here, R³ has, for example, the meanings given above in group 1.

Group 86

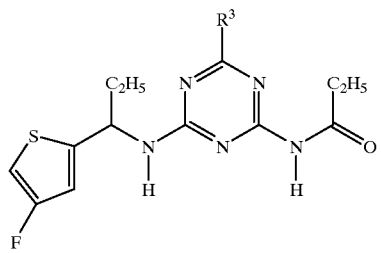
(I-86)

Here, R³ has, for example, the meanings given above in group 1.

Group 87

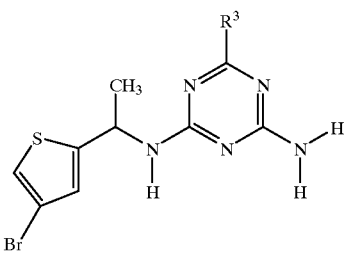
(I-87)

Here, R³ has, for example, the meanings given above in group 1.

Group 88

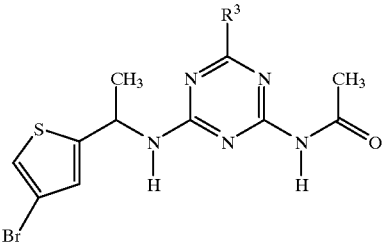
(I-88)

Here, R³ has, for example, the meanings given above in group 1.

Group 89

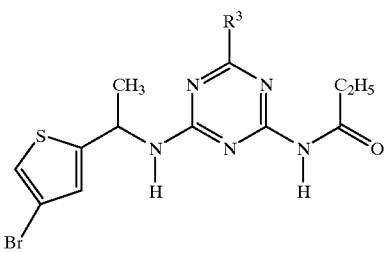
(I-89)

Here, R³ has, for example, the meanings given above in group 1.

Group 90

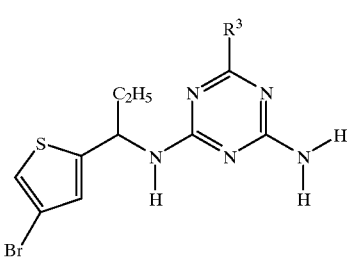
(I-90)

Here, R³ has, for example, the meanings given above in group 1.

Group 91

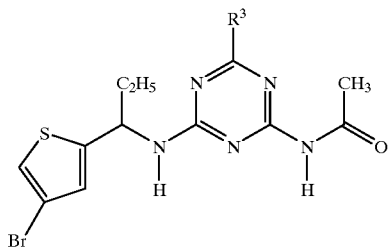
(I-91)

Here, R³ has, for example, the meanings given above in group 1.

Group 92

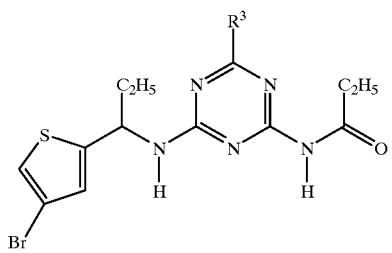
(I-92)

Here, R³ has, for example, the meanings given above in group 1.

Group 93

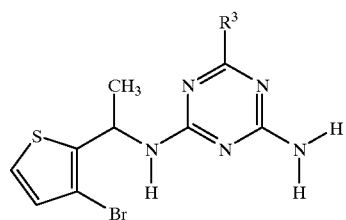
(I-93)

Here, R³ has, for example, the meanings given above in group 1.

Group 94

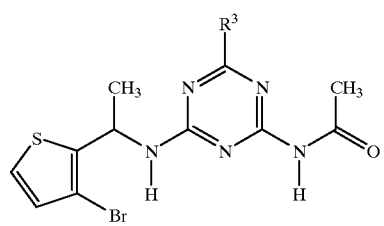
(I-94)

Here, R³ has, for example, the meanings given above in group 1.

Group 95

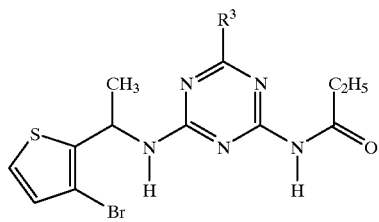
(I-95)

Here, R³ has, for example, the meanings given above in group 1.

Group 96

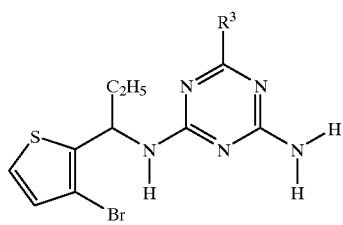
(I-96)

Here, R³ has, for example, the meanings given above in group 1.

Group 97

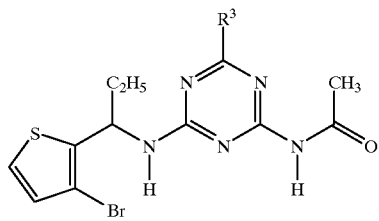
(I-97)

Here, R³ has, for example, the meanings given above in group 1.

Group 98

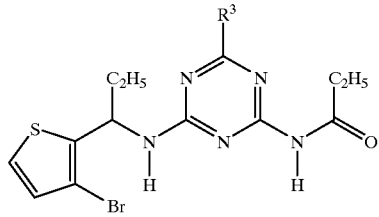
(I-98)

Here, R³ has, for example, the meanings given above in group 1.

Group 99

(I-99)

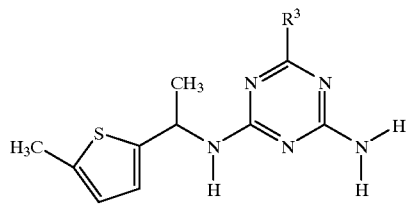

Here, R³ has, for example, the meanings given above in group 1.

Group 100

(I-100)

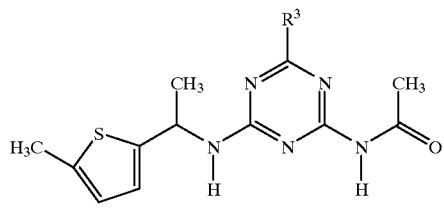

Here, R³ has, for example, the meanings given above in group 1.

Group 101

(I-101)

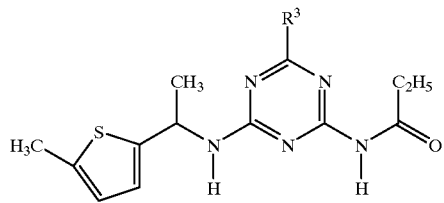

Here, R³ has, for example, the meanings given above in group 1.

Group 102

(I-102)

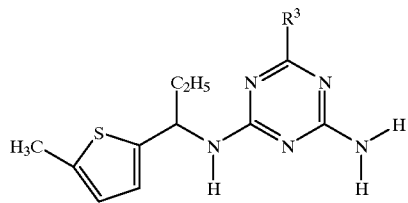

Here, R³ has, for example, the meanings given above in group 1.

Group 103

(I-103)

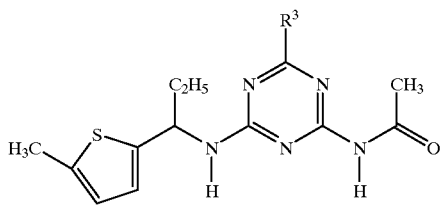

Here, R³ has, for example, the meanings given above in group 1.

Group 104

(I-104)

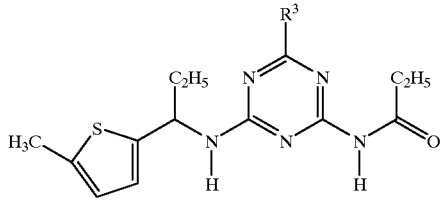

Here, R³ has, for example, the meanings given above in group 1.

Group 105

(I-105)

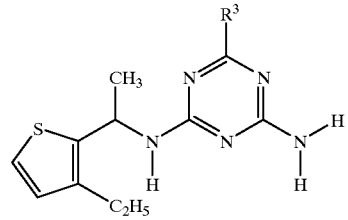

Here, R³ has, for example, the meanings given above in group 1.

Group 106

(I-106)

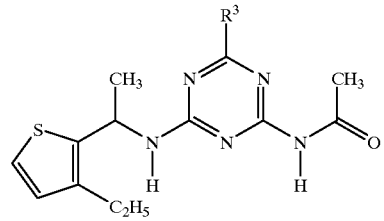

Here, R³ has, for example, the meanings given above in group 1.

Group 107

(I-107)

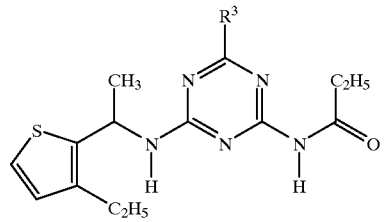

Here, R³ has, for example, the meanings given above in group 1.

Group 108

(I-108)

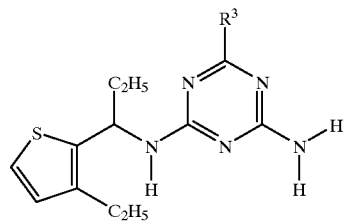

Here, R³ has, for example, the meanings given above in group 1.

Group 109

(I-109)

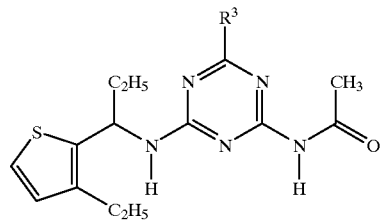

Here, R³ has, for example, the meanings given above in group 1.

Group 110

(I-110)

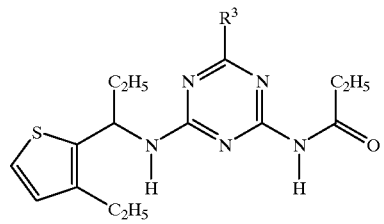

Here, R³ has, for example, the meanings given above in group 1.

Group 111

(I-111)

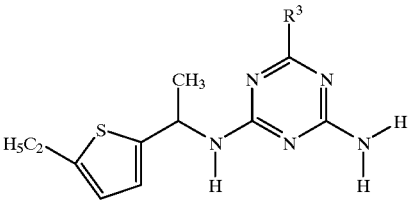

Here, R³ has, for example, the meanings given above in group 1.

Group 112

(I-112)

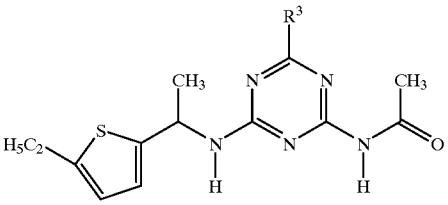

Here, R³ has, for example, the meanings given above in group 1.

Group 113

(I-113)

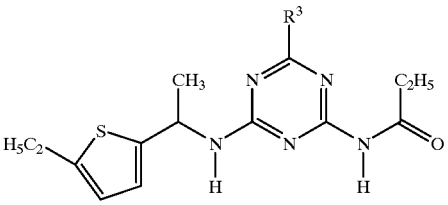

Here, R³ has, for example, the meanings given above in group 1.

Group 114

(I-114)

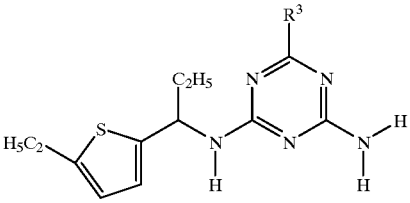

Here, R³ has, for example, the meanings given above in group 1.

Group 115

(I-115)

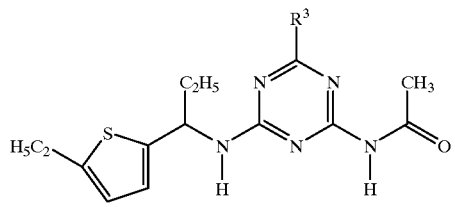

Here, R³ has, for example, the meanings given above in group 1.

Group 116

(I-116)

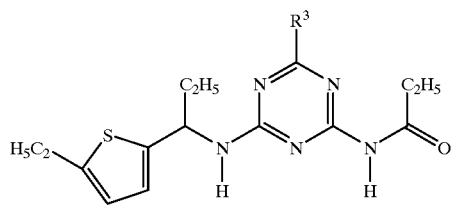

Here, R³ has, for example, the meanings given above in group 1.

Group 117

(I-117)

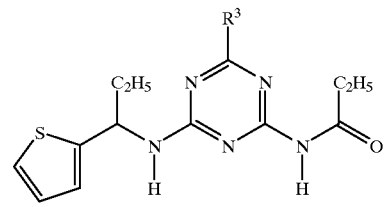

Here, R³ has, for example, the meanings given above in group 1.

Group 118

(I-118)

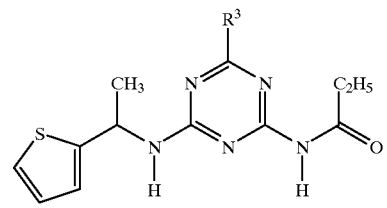

Here, R³ has, for example, the meanings given above in group 1.

Group 119

(I-119)

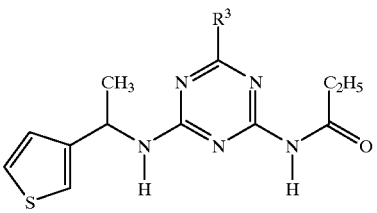

Here, R³ has, for example, the meanings given above in group 1.

Group 120

(I-120)

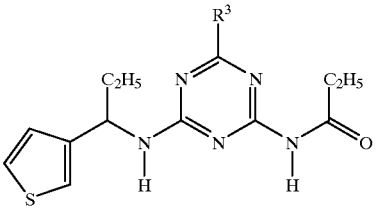

Here, R³ has, for example, the meanings given above in group 1.

Group 121

(I-121)

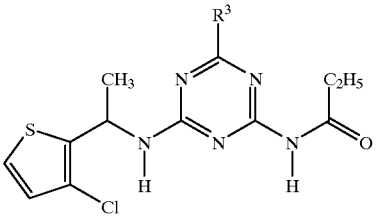

Here, R³ has, for example, the meanings given above in group 1.

Group 122

(I-122)

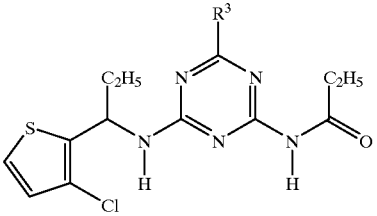

Here, R³ has, for example, the meanings given above in group 1.

Group 123

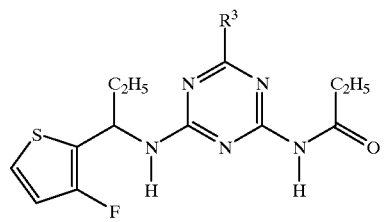
(I-123)

Here, R³ has, for example, the meanings given above in group 1.

Group 124

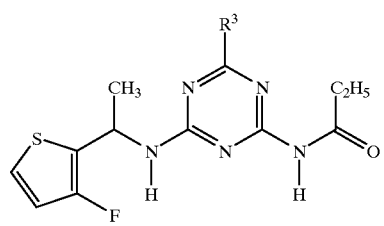
(I-124)

Here, R³ has, for example, the meanings given above in group 1.

Group 125

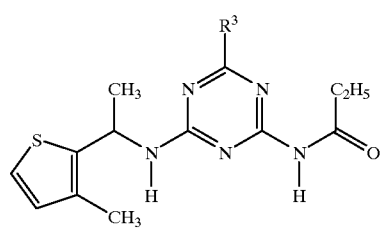
(I-125)

Here, R³ has, for example, the meanings given above in group 1.

Group 126

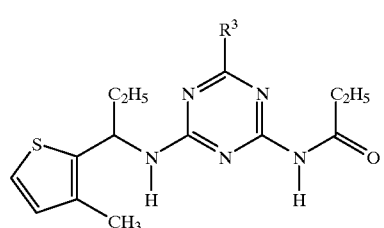
(I-126)

Here, R³ has, for example, the meanings given above in group 1.

Group 127

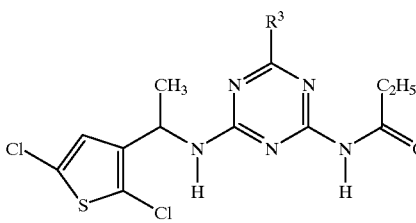
(I-127)

Here, R³ has, for example, the meanings given above in group 1.

Group 128

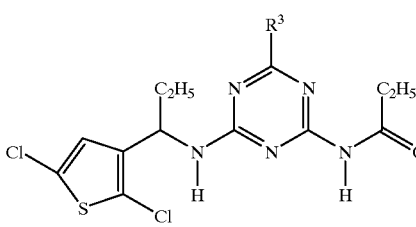
(I-128)

Here, R³ has, for example, the meanings given above in group 1.

Group 129

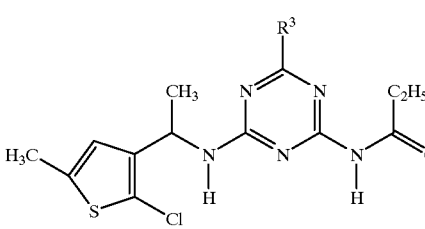
(I-129)

Here, R³ has, for example, the meanings given above in group 1.

Group 130

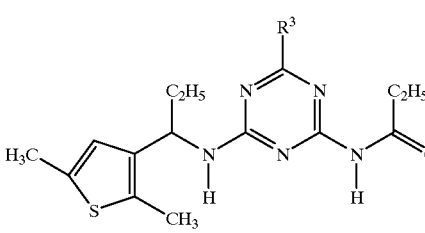
(I-130)

Here, R³ has, for example, the meanings given above in group 1.

Group 131

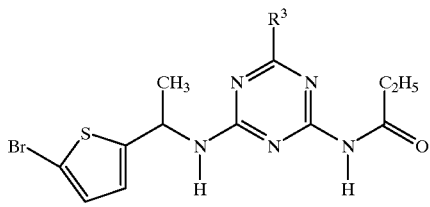
(I-131)

Here, R³ has, for example, the meanings given above in group 1.

Group 132

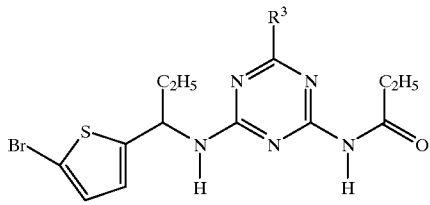
(I-132)

Here, R³ has, for example, the meanings given above in group 1.

Group 133

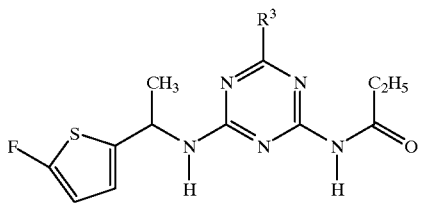
(I-133)

Here, R³ has, for example, the meanings given above in group 1.

Group 134

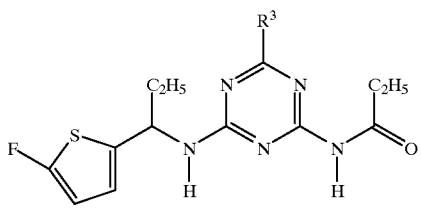
(I-134)

Here, R³ has, for example, the meanings given above in group 1.

Using, for example, 1-(1-thien-3-yl-propyl)-biguanide and methyl trifluoroacetate as starting materials, the course of the reaction in the process (a) according to the invention can be illustrated by the following formula scheme:

Using, for example, 2-amino-4-(1-methyl-2,2,2-trifluoro-ethyl)-6-(1-thien-2-yl-ethylamino)-1,3,5-triazine and acetyl chloride as starting materials, the course of the reaction in the process (b) according to the invention can be illustrated by the following formula scheme:

The formula (II) provides a general definition of the substituted biguanides to be used as starting materials in the process (a) according to the invention for preparing compounds of the formula (I). In the formula (II), $R^1$, $R^2$, $R^4$ and $R^5$ preferably or in particular have those meanings which have already been mentioned above, in connection with the description of the compounds of the formula (I) according to the invention, as being preferred or as being particularly preferred for $R^1$, $R^2$, $R^4$ and $R^5$.

Suitable acid adducts of compounds of the formula (II) are their addition products with protic acids, such as, for example, hydrogen chloride, hydrogen bromide, sulphuric acid, methanesulphonic acid, benzenesulphonic acid and p-toluenesulphonic acid.

Except for 1-(2-furyl-methyl)-biguanide (hydrochloride) and 1-(2-thienyl-methyl)-biguanide (hydrochloride)—cf. J. Am. Chem. Soc. 81 (1959), 3728–3736 and U.S. Pat. No. 2,961,377—, the starting materials of the general formula (II) have hitherto not been disclosed in the literature; except for 1-(2-furyl-methyl)-biguanide (hydrochloride) and 1-(2-thienyl-methyl)-biguanide (hydrochloride) they also form, as novel substances, part of the subject-matter of the present application.

The substituted biguanides of the general formula (II) are obtained when amines of the general formula (V)

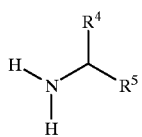

(V)

in which
R[4] and R[5] are as defined above—and/or acid adducts of compounds of the general formula (V), such as, for example, the hydrochlorides—are reacted with cyanoguanidines of the general formula (VI)

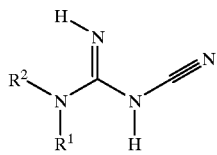

(VI)

in which
R[1] and R[2] are as defined above, if appropriate in the presence of a reaction auxiliary, such as, for example, hydrogen chloride, and if appropriate in the presence of a diluent, such as, for example, n-decane, toluene or 1,2-dichloro-benzene, at temperatures between 100° C. and 200° C. (cf. the Preparation Examples).

The compounds of the formulae (V) and (VI) are known and/or can be prepared by processes known per se.

The formula (III) provides a general definition of the alkoxycarbonyl compounds further to be used as starting materials in the process (a) according to the invention for preparing compounds of the formula (I). In the formula (III), R[3] preferably or in particular has that meaning which has already been mentioned above, in connection with the description of the compounds of the formula (I) according to the invention, as being preferred or as being particularly preferred for R[3]; R preferably represents alkyl having 1 to 4 carbon atoms, in particular methyl or ethyl.

The starting materials of the formula (III) are known chemicals for synthesis.

The formula (Ia) provides a general definition of the 2,4-diamino-1,3,5-triazines to be used as starting materials in the process (b) according to the invention for preparing compounds of the formula (I). In the formula (Ia), R[1], R[3], R[4] and R[5] preferably or in particular have those meanings which have already been mentioned above, in connection with the description of the compounds of the formula (I) according to the invention, as being preferred or as being particularly preferred for R[1], R[3], R[4] and R[5].

As novel compounds, the starting materials of the general formula (Ia) also form part of the subject-matter of the present application; they can be prepared according to process (a).

The formula (IV) provides a general definition of the alkylating or acylating agents further to be used as starting materials in the process (b) according to the invention for preparing compounds of the formula (I). In the formula (IV), R[2] preferably or in particular has that meaning which has already been mentioned above, in connection with the description of the compounds of the formula (I) according to the invention, as being preferred or as being particularly preferred for R[2]; X preferably represents fluorine, chlorine, bromine, iodine, methoxy, ethoxy, acetyl, methoxysulphonyloxy or ethoxysulphonyloxy.

The starting materials of the general formula (IV) are known chemicals for synthesis.

If appropriate, the processes according to the invention for preparing the compounds of the formula (I) are carried out using a reaction auxiliary. Suitable reaction auxiliaries for the processes (a) and (b) are the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2,2,2]-octane (DABCO), 1,5-diazabicyclo[4,3,0]-non-5-ene (DBN), or 1,8-diazabicyclo[5,4,0]-undec-7-ene (DBU).

Suitable diluents for carrying out the processes (a) and (b) according to the invention are, if appropriate, inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as methyl isopropyl ketone or methyl isobutyl ketone; nitrites, such as acetonitrile, propionitrile or butyronitrile; amides, such as N,N-dimethylformamide, N,N-dimethylacetamide, N-methylformanilide, N-methyl-pyrrolidone or hexamethylphosphoric triamide; esters, such as methyl acetate or ethyl acetate; sulphoxides, such as dimethyl sulphoxide; alcohols, such as methanol, ethanol, n- or i-propanol, ethylene glycol monomethyl ether, ethylene glycol monoethyl ether, diethylene glycol monomethyl ether, diethylene glycol monoethyl ether, mixtures thereof with water or pure water.

When carrying out the processes (a) and (b) according to the invention, the reaction temperatures can be varied within a relatively wide range. In general, the processes are carried out at temperatures between 0° C. and 180° C., preferably between 10° C. and 150° C.

The processes (a) and (b) according to the invention are generally carried out under atmospheric pressure. However, it is also possible to carry out the processes according to the invention under elevated or reduced pressure—in general between 0.1 bar and 10 bar.

For carrying out the processes according to the invention, the starting materials are generally employed in approximately equimolar amounts. However, it is also possible for one of the components to be used in a relatively large excess.

The reaction is generally carried out in a suitable diluent in the presence of a reaction auxiliary, and the reaction mixture is generally stirred at the required temperature for several hours. Work-up is carried out by customary methods (cf. the Preparation Examples).

The active compounds according to the invention can be used as defoliants, desiccants, haulm killers and, especially, as weed killers. By weeds in the broadest sense there are to be understood all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodiun, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbrstylis, Sagittaria, Eleocharis, Scirpus, Paspalum, Ischaemum, Sphenoclea, Dactyloctenium, Agrostis, Alopecurus, Apera, Phalaris, Aegilops.

Monocotyledonous crops of the genera: Oryza, Zea, Triticum, Hordeum, Avena, Secale, Sorghum, Panicum, Saccharum, Ananas, Asparagus, Allium.

However, the use of the active compounds according to the invention is in no way restricted to these genera, but also extends in the same manner to other plants.

Depending on the concentration, the compounds are suitable for total weed control, for example on industrial terrain and rail tracks and on paths and areas with or without tree growth. Equally, the compounds can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns and turf and pastures and for selective weed control in annual crops.

The compounds of the formula (I) according to the invention are particularly suitable for selective control of monocotyledonous and dicotyledonous weeds in monocotyledonous crops, both by the pre-emergence and by the post-emergence method.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formulations are prepared in a known manner, for example by mixing the active compounds with extenders, that is to say liquid solvents and/or solid carriers, optionally with the use of surfactants, that is to say emulsifiers and/or dispersants and/or foam formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use dyestuffs, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, for example acetochlor, acifluorfen(-sodium), aclonifen, alachlor, alloxydim(-sodium), ametryne, amidochlor, amidosulfuron, asulam, atrazine, azimsulfuron, benazolin, benfuresate, bensulfuron(-methyl), bentazone, benzofenap, benzoylprop(-ethyl), bialaphos, bifenox, bromobutide, bromofenoxim, bromoxynil, butachlor, butylate, cafenstrole, carbetamide, chlomethoxyfen, chloramben, chloridazon, chlorimuron(-ethyl), chlornitrofen, chlorsulfuron, chlorotoluron, cinmethylin, cinosulfuron, clethodim, clodinafop(-propargyl), clomazone, clopyralid, clopyrasulfuron, cloransulam (-methyl), cumyluron, cyanazine, cycloate, cyclosulfamuron, cycloxydim, cyhalofop(-butyl), 2,4-D, 2,4-DB, 2,4-DP, desmedipham, diallate, dicamba, diclofop (-methyl), difenzoquat, diflufenican, dimefuron, dimepiperate, dimethachlor, dimethametryn, dimethenamid, dinitramine, diphenamid, diquat, dithiopyr, diuron, dymron, EPTC, esprocarb, ethalfluralin, ethametsulfuron(-methyl), ethofumesate, ethoxyfen, etobenzanid, fenoxaprop(-ethyl), flamprop(-isopropyl), flamprop(-isopropyl-L), flamprop (-methyl), flazasulfuron, fluazifop(-butyl), flumetsulam, flumiclorac(-pentyl), flumioxazin, flumipropyn, fluometuron, fluorochloridone, fluoroglycofen(-ethyl), flupoxam, flupropacil, flurenol, fluridone, fluroxypyr, flurprimidol, flurtamone, fomesafen, glufosinate (-ammonium), glyphosate(-isopropylammonium), halosafen, haloxyfop(-ethoxyethyl), hexazinone, imazamethabenz (-methyl), imazamethapyr, imazamox, imazapyr, imazaquin, imazethapyr, imazosulfuron, ioxynil, isopropalin, isoproturon, isoxaben, isoxaflutole, isoxapyrifop, lactofen, lenacil, linuron, MCPA, MCPP, mefenacet, metamitron, metazachlor, methabenzthiazuron, metobenzuron, metobromuron, metolachlor, metosulam, metoxuron, metribuzin, metsulfuron(-methyl), molinate, monolinuron, naproanilide, napropamide, neburon, nicosulfuron, norflurazon orbencarb, oryzalin, oxadiazon, oxyfluorfen, paraquat, pendimethalin, phenmedipham, piperophos, pretilachlor, primisulfuron(-methyl), prometryn, propachlor, propanil, propaquizafop, propyzamide, prosulfocarb, prosulfuron, pyrazolate, pyrazosulfuron(-ethyl), pyrazoxyfen, pyributicarb, pyridate, pyrithiobac(-sodium), quinchlorac, quinmerac, quizalofop (-ethyl), quizalofop(-p-tefuryl), rimsulfuron, sethoxydim, simazine, simetryn, sulcotrione, sulfentrazone, sulfometuron(-methyl), sulfosate, tebutam, tebuthiuron, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention can be seen from the examples below.

Preparation Examples

EXAMPLE 1

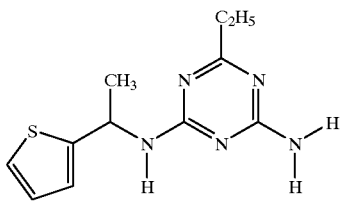

(Process (a))

With stirring, 2.4 g (44 mmol) of sodium methoxide are added to a mixture of 10.0 g (40 mmol) of 1-(1-thien-2-yl-ethyl)-biguanide hydrochloride, 4.5 g (40 mmol) of methyl propionate and 80 ml of methanol, and the reaction mixture is stirred at room temperature (about 20° C.) for 15 hours. The mixture is then diluted with diethyl ether to about twice its volume, and the organic phase is washed twice with water, dried with sodium sulphate and filtered. From the filtrate, the solvent is carefully distilled off under water pump vacuum.

This gives 3.2 g (32% of theory) of 2-amino-4-ethyl-6-(1-thien-2-yl-ethylamino)-1,3,5-triazine as an amorphous material.

EXAMPLE 2

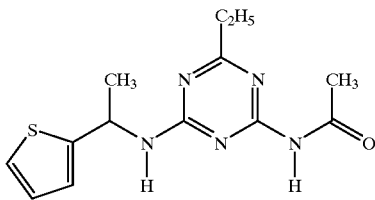

(Process (b))

A mixture of 4.0 g (16 mmol) of 2-amino-4-ethyl-6-(1-thien-2-yl-ethylamino)-1,3,5-triazine and 35 ml of acetic anhydride is stirred at from 120° C. to 130° C. for 2 hours. After cooling to room temperature, the mixture is diluted with 100 ml of water and stirred for one hour. The crystalline product is then isolated by filtration with suction.

This gives 2.1 g (45% of theory) of 2-acetylamino-4-ethyl-6-(1-thien-2-yl-ethyl-amino)-1,3,5-triazine of melting point 153° C.

Analogously to the Preparation Examples 1 and 2 and in accordance with the general description of the preparation processes according to the invention, it is also possible to prepare, for example, the compounds of the formula (I) listed in Table 1 below.

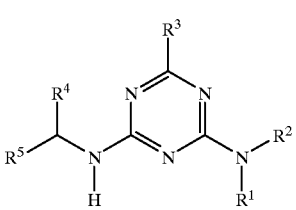

(I)

TABLE 1

Examples of the compounds of the formula (I)

| Ex. No. | R¹ | R² | R³ | R⁴ | R⁵ | Physical data |
|---|---|---|---|---|---|---|
| 3 | H | H | H | CH₃ | 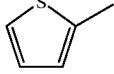 | m.p.: 152° C. |
| 4 | H | H | —CH₂OCH₃ | CH₃ | 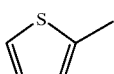 | m.p.: 158° C. |
| 5 | H | H | CHCl₂ | CH₃ | 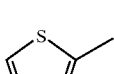 | m.p.: 135° C. |
| 6 | H | H | CHClCH₃ | CH₃ | 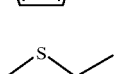 | m.p.: 125° C. |
| 7 | H | H | CCl₂CH₃ | CH₃ | 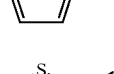 | (amorphous) |
| 8 | H | H | CHFCF₃ | CH₃ | 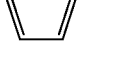 | (amorphous) |
| 9 | H | —CO—CH₃ | CHCl₂ | CH₃ | 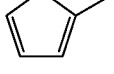 | m.p.: 113° C. |
| 10 | H | —CO—CH₃ | CHClCH₃ | CH₃ | 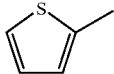 | m.p.: 133° C. |
| 11 | H | H | C₂H₅ | C₂H₅ | 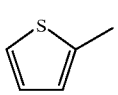 | (amorphous) |
| 12 | H | H | —CH₂OCH₃ | C₂H₅ | 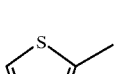 | (amorphous) |
| 13 | H | H | CHCl₂ | C₂H₅ | 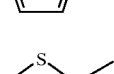 | (amorphous) |
| 14 | H | H | CHClCH₃ | C₂H₅ | 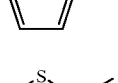 | (amorphous) |
| 15 | H | H | CHFCH₃ | C₂H₅ | 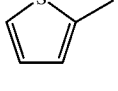 | (amorphous) |
| 16 | H | H | CHFCF₃ | C₂H₅ | 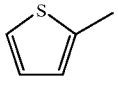 | (amorphous) |

TABLE 1-continued

Examples of the compounds of the formula (I)

| Ex. No. | R¹ | R² | R³ | R⁴ | R⁵ | Physical data |
|---|---|---|---|---|---|---|
| 17 | H | H | CCl₂CH₃ | C₂H₅ | 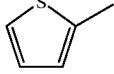 | (amorphous) |
| 18 | H | —CO—CH₃ | C₂H₅ | C₂H₅ | 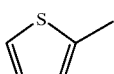 | (amorphous) |
| 19 | H | —CO—CH₃ | —CH₂OCH₃ | C₂H₅ | 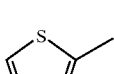 | (amorphous) |
| 20 | H | —CO—CH₃ | CHCl₂ | C₂H₅ | 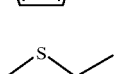 | m.p.: 131° C. |
| 21 | H | —CO—CH₃ | CHClCH₃ | C₂H₅ | 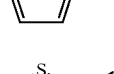 | (amorphous) |
| 22 | H | —CO—CH₃ | CHFCH₃ | C₂H₅ | 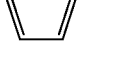 | (amorphous) |
| 23 | H | —CO—CH₃ | CHFCF₃ | C₂H₅ | 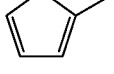 | m.p.: 147° C. |
| 24 | H | —CO—CH₃ | CCl₂CH₃ | C₂H₅ | 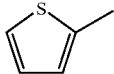 | m.p.: 113° C. |
| 25 | H | H | CF₃ | CH₃ | 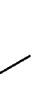 | (amorphous) |
| 26 | H | H | CHF₂ | CH₃ |  | (amorphous) |
| 27 | H | H | CF(CH₃)₂ | CH₃ |  | (amorphous) |
| 28 | H | H | C₂H₅ | CH₃ |  | (amorphous) |
| 29 | H | H | H | CH₃ |  | (amorphous) |
| 30 | H | H | CHFCH₃ | CH₃ |  | (amorphous) |

TABLE 1-continued

Examples of the compounds of the formula (I)

| Ex. No. | R¹ | R² | R³ | R⁴ | R⁵ | Physical data |
|---|---|---|---|---|---|---|
| 31 | H | H | CH$_2$OCH$_3$ | CH$_3$ |  | (amorphous) |
| 32 | H | H | CH$_2$SCH$_3$ | CH$_3$ |  | (amorphous) |
| 33 | H | H | CH$_2$CN | CH$_3$ |  | (amorphous) |
| 34 | H | H | C$_3$H$_7$-n | CH$_3$ |  | m.p.: 160° C. |
| 35 | H | H | C$_3$H$_7$-i | CH$_3$ |  | (amorphous) |
| 36 | H | H | 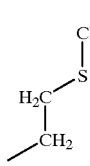 | CH$_3$ |  | (amorphous) |
| 37 | H | H | 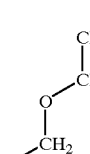 | CH$_3$ |  | (amorphous) |
| 38 | H | H | 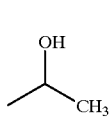 | CH$_3$ |  | (amorphous) |
| 39 | H | H | CF(CH$_3$)$_2$ | C$_2$H$_5$ |  | (amorphous) |
| 40 | H | H | CHFCH$_3$ | C$_2$H$_5$ | 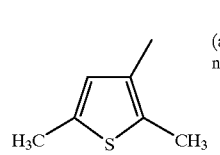 | (amorphous)<br>n$_D^{20}$: 1.5030 |
| 41 | H | H | CF(CH$_3$)$_2$ | C$_2$H$_5$ | 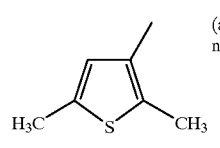 | (amorphous)<br>n$_D^{20}$: 1.5371 |
| 42 | H | H | CHFCH$_3$ | CH$_3$ | 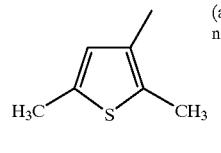 | (amorphous)<br>n$_D^{20}$: 1.4923 |

TABLE 1-continued

Examples of the compounds of the formula (I)

| Ex. No. | R¹ | R² | R³ | R⁴ | R⁵ | Physical data |
|---|---|---|---|---|---|---|
| 43 | H | H | CF(CH₃)₂ | CH₃ | 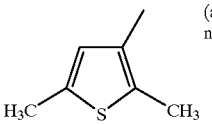 | (amorphous) $n_D^{20}$: 1.4862 |
| 44 | H | H | CF(CH₃)₂ | CH₃ | 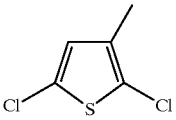 | (amorphous) |
| 45 | H | H | CHFCH₃ | CH₃ | 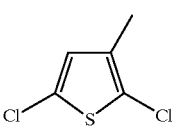 | (amorphous) |
| 46 | H | H | CHFCH₃ | C₂H₅ | 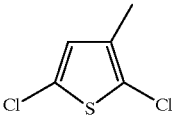 | (amorphous) |
| 47 | H | H | CF(CH₃)₂ | C₂H₅ | 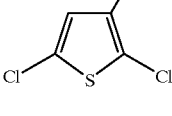 | (amorphous) |
| 48 | H | —CO—CH₃ | CF(CH₃)₂ | CH₃ | 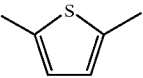 | m.p.: 132° C. |
| 49 | H | —CO—C₂H₅ | CF(CH₃)₂ | CH₃ | 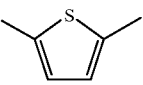 | m.p.: 118° C. |
| 50 | H | —CO—CH₃ | C₂H₅ | CH₃ | 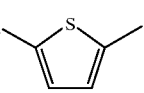 | m.p.: 148° C. |
| 51 | H | —CO—C₂H₅ | C₂H₅ | CH₃ | 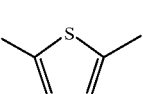 | m.p.: 134° C. |
| 52 | H | —CO—CH₃ | CHFCH₃ | CH₃ | 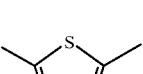 | m.p.: 152° C. |
| 53 | H | —CO—C₂H₅ | CHFCH₃ | CH₃ | 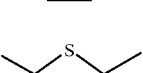 | m.p.: 133° C. |
| 54 | H | H | CHFCH₃ | CH₃ | 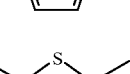 | (amorphous) |

TABLE 1-continued

Examples of the compounds of the formula (I)

| Ex. No. | R$^1$ | R$^2$ | R$^3$ | R$^4$ | R$^5$ | Physical data |
|---|---|---|---|---|---|---|
| 55 | H | H | CH=C(CH$_3$)– (H, CH$_3$ cis) | C$_2$H$_5$ | 2-thienyl | (amorphous) |
| 56 | H | H | CH=C(CH$_3$)– (H, CH$_3$ trans) | C$_2$H$_5$ | 2-thienyl | (amorphous) |
| 57 | H | H | CHFCH$_3$ | CH$_3$ | 3-thienyl | (amorphous) |
| 58 | H | H | CF(CH$_3$)$_2$ | CH$_3$ | 3-thienyl | (amorphous) |
| 59 | H | H | CHClCH$_3$ | CH$_3$ | 3-thienyl | (amorphous) |
| 60 | H | —CO—CH$_3$ | CHFCH$_3$ | CH$_3$ | 3-thienyl | m.p.: 121° C. |
| 61 | H | —CO—C$_2$H$_5$ | CF(CH$_3$)$_2$ | CH$_3$ | 3-thienyl | (amorphous) |
| 62 | H | H | CHFCH$_3$ | CH$_3$ | 3-methyl-2-thienyl | (amorphous) |
| 63 | H | H | CF(CH$_3$)$_2$ | CH$_3$ | 3-methyl-2-thienyl | (amorphous) |
| 64 | H | H | CHFCH$_3$ | C$_2$H$_5$ | 3-methyl-2-thienyl | (amorphous) |

TABLE 1-continued

Examples of the compounds of the formula (I)

| Ex. No. | R¹ | R² | R³ | R⁴ | R⁵ | Physical data |
|---|---|---|---|---|---|---|
| 65 | H | H | $CF(CH_3)_2$ | $C_2H_5$ | 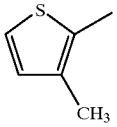 | (amorphous) |

Starting Materials of the Formula (II)

Example (II-1)

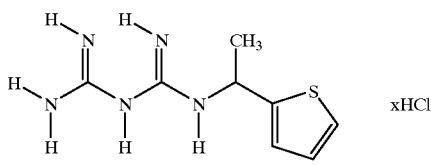

60 g of 33% strength aqueous hydrochloric acid are added to 63.5 g (0.50 mol) of 1-(thien-2-yl)-ethylamine and 100 ml of methanol, and the mixture is concentrated under water pump vacuum. Toluene is added to the residue, and the mixture is concentrated once more. 42 g (0.50 mol) of cyanoguanidine are added to the remaining residue, and the mixture is (as a melt) kept at from 150° C. to 160° C. for 3 hours. On cooling, the product solidifies, forming a glass.

This gives 122.5 g (99% of theory) of 1-(1-thien-2-yl-ethyl)-biguanide hydrochloride.

Analogously to Example (II-1), it is also possible to obtain 1-(1-thien-2-yl-propyl)-biguanide hydrochloride (II-2), likewise as a glasslike material; furthermore also 1-(1-thien-3-yl-ethyl)-biguanide hydrochloride (II-3) and 1-[1-(3-methyl-thien-2-yl)-ethyl]-biguanide hydrochloride (II-4), in each case as grasslike materials.

Precursors of the Formula (V)

Example (V-1)

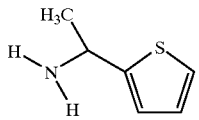

Step 1

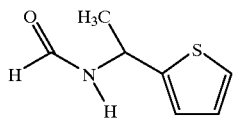

At from 140° C. to 160° C., 150 ml of formic acid are added dropwise with stirring to a mixture of 100 g (0.79 mol) of 2-acetyl-thiophene and 300 ml of formamide, and the reaction mixture is stirred at 160° C. for 2 hours. After cooling to room temperature, the mixture is diluted with toluene to about twice its volume, washed twice with water, dried with sodium sulphate and filtered. From the filtrate, the solvent is carefully distilled off under water pump vacuum.

This gives 78 g (64% of theory) of N-(1-thien-2-yl-ethyl)-formamide as an amorphous residue.

Step 2

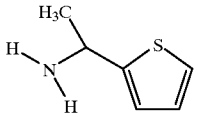

A mixture of 75 g (0.48 mol) of N-(1-thien-2-yl-ethyl)-formamide, 120 ml of conc. hydrochloric acid and 50 ml of water is heated under reflux for 3 hours and then concentrated under water pump vacuum. The residue is shaken with water/methylene chloride, and the aqueous phase is made alkaline using 2N aqueous sodium hydroxide solution and shaken with toluene. The toluene phase is dried with sodium sulphate and filtered. The filtrate is worked up by distillation under reduced pressure.

This gives 24.8 g (41% of theory) of 1-(thien-2-yl)-ethylamine of boiling point 40° C. at 0.8 mbar.

Analogously to Example (V-1), it is also possible to obtain 1-(thien-2-yl)-propyl-amine (V-2) of boiling point 52° C. at 0.7 mbar.

Use Examples

Example A

Pre-emergence Test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound such that the particular amounts of active compound desired are applied per unit area. The concentration of the spray liquor is chosen so that the particular amounts of active compound desired are applied in 1000 l of water/ha.

After three weeks, the degree of damage to the plants is rated in % damage in comparison with the development of the untreated control.

The figures denote:

0%=no effect (like untreated control)

100%=total destruction

In this test, for example, the compounds of Preparation Example 15 and 22 exhibit strong action against weeds, and they are tolerated very well by crop plants, such as, for example, maize.

"a.i"—Active Ingredient

TABLE A

Pre-emergence test/greenhouse

| Active compound of Preparation Ex. No. | Application rate (g of ai./ha) | Maize | Setaria | Amaranthus | Galium | Sinapis |
|---|---|---|---|---|---|---|
| 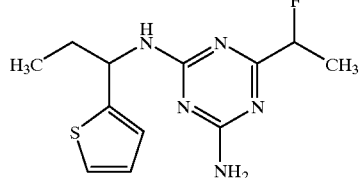 (15) | 1000 | 0 | 90 | 100 | 100 | — |
| 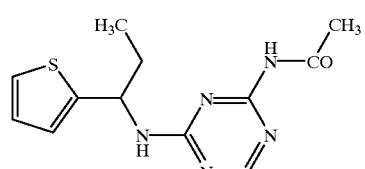 (22) | 1000 | 0 | 100 | 95 | 100 | 100 |

Example B

Post-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants having a height of 5–15 cm are sprayed with the preparation of active compound such that the particular amounts of active compound desired are applied per unit area. The concentration of the spray liquor is chosen so that the particular amounts of active compound desired are applied in 1000 l of water/ha.

After three weeks, the degree of damage to the plants is rated in % damage in comparison with the development of the untreated control.

The figures denote:

0%=no effect (like untreated control)

100%=total destruction

In this test, for example, the compounds of Preparation Example 1, 2, 5, 6, 11, 13, 14, 15, 16, 18, 20, 21, 22 and 24 exhibit strong action against weeds, and some of them are tolerated well by crop plants, such as, for example, maize.

TABLE B

Post-emergence test/greenhouse

| Active compound of Preparation Ex. No. | Application rate (g of ai./ha) | Maize | Setaria | Abutilon | Amaranthus | Sinapis | Xanthium |
|---|---|---|---|---|---|---|---|
| 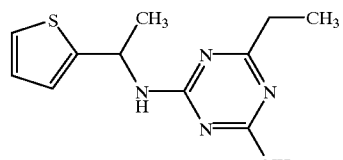 (1) | 1000 | 30 | — | 100 | 100 | 100 | |

TABLE B-continued

| | Post-emergence test/greenhouse | | | | | | |
|---|---|---|---|---|---|---|---|
| Active compound of Preparation Ex. No. | Application rate (g of ai./ha) | Maize | Setaria | Abutilon | Amaranthus | Sinapis | Xanthium |
| (2) | 1000 | 0 | 90 | 100 | 100 | 100 | |
| (11) | 1000 | 30 | 100 | 100 | 100 | 100 | |
| (14) | 1000 | 30 | 100 | 100 | 100 | 100 | |
| (15) | 1000 | 0 | 100 | 100 | 100 | 100 | |
| (16) | 1000 | 10 | 100 | 100 | 100 | 100 | |

TABLE B-continued
| | Post-emergence test/greenhouse | | | | | | |
|---|---|---|---|---|---|---|---|
| Active compound of Preparation Ex. No. | Application rate (g of ai./ha) | Maize | Setaria | Abutilon | Amaranthus | Sinapis | Xanthium |
| 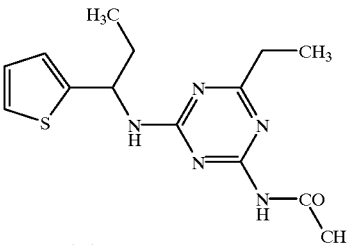 (18) | 1000 | 20 | 100 | 100 | 100 | 100 | |
| 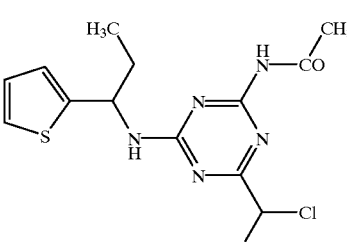 (20) | 1000 | 0 | 100 | 100 | 100 | 100 | |
| 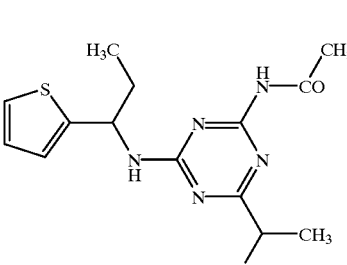 (21) | 1000 | 0 | 100 | 100 | 100 | 100 | |
| 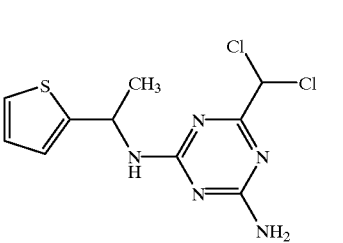 (5) | 1000 | | 90 | 100 | 100 | 100 | |
| 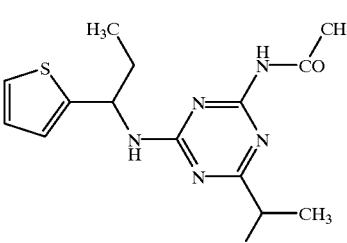 (22) | 1000 | | 100 | 100 | 100 | 100 | |

TABLE B-continued

Post-emergence test/greenhouse

| Active compound of Preparation Ex. No. | Application rate (g of ai./ha) | Maize | Setaria | Abutilon | Amaranthus | Sinapis | Xanthium |
|---|---|---|---|---|---|---|---|
| (6) | 1000 | 0 | — | 100 | 100 | — | 100 |
| (13) | 1000 | 10 | 100 | — | 100 | 100 | 80 |
| (24) | 1000 | 100 | | 100 | 100 | 100 | 100 |

What is claimed is:

1. A 2,4-diamino-1,3,5-triazine of the formula (I)

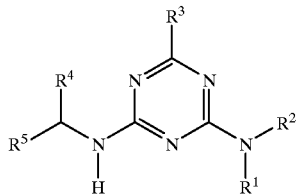

wherein
- $R^1$ represents hydrogen or represents unsubstituted or cyano-, halogen- or $C_1$–$C_4$-alkoxy-substituted alkyl having 1 to 6 carbon atoms,
- $R^2$ represents hydrogen, or represents unsubstituted or cyano-, halogen- or $C_1$–$C_4$-alkoxy-substituted alkyl having 1 to 6 carbon atoms or represents the grouping —CO—$R^6$,
- $R^3$ represents unsubstituted or halogen-substituted alkyl having 1 to 6 carbon atoms, or represents unsubstituted or halogen-substituted cycloalkyl having 3 to 6 carbon atoms,
- $R^4$ represents unsubstituted or cyano-, halogen- or $C_1$–$C_4$-alkoxy-substituted alkyl having 1 to 6 carbon atoms, or represents unsubstituted or cyano-, halogen- or $C_1$–$C_4$-alkyl-substituted cycloalkyl having 3 to 6 carbon atoms,

- $R^5$ represents one of the groupings below,

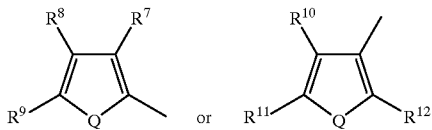

- $R^6$ represents hydrogen or represents unsubstituted or cyano-, halogen- or $C_1$–$C_4$-alkoxy-substituted alkyl, alkoxy, alkylamino or dialkylamino having in each case 1 to 6 carbon atoms in the alkyl groups or represents unsubstituted or halogen-substituted alkenyl having 2 to 6 carbon atoms,
- $R^7$ represents hydrogen, nitro, cyano, carbamoyl, thiocarbamoyl, sulphamoyl, halogen, or represents unsubstituted or cyano-, halogen- or $C_1$–$C_4$-alkoxy-substituted alkyl, alkoxy, alkylthio, alkylsulphinyl, alkylsulphonyl, alkylcarbonyl, alkoxycarbonyl, alkylaminosulphonyl or dialkylaminosulphonyl having in each case 1 to 6 carbon atoms in the alkyl groups, or represents unsubstituted or cyano-, halogen- or $C_1$–$C_4$- alkyl-substituted cycloalkyl, or represents unsubstituted or nitro-, cyano-, carbamoyl-, thiocarbamoyl-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, phenoxy or phenylthio, $R^8$ represents hydrogen, nitro, cyano, carbamoyl, thiocarbamoyl, sulphamoyl, fluorine, bromine, or represents cyano-, halogen- or $C_1$–$C_4$-alkoxy-substituted methyl, or represents unsubstituted or cyano-, halogen- or $C_1$–$C_4$-alkoxy-substituted alkyl having 2 to 6 carbon atoms, or represents unsubstituted or cyano-, halogen- or $C_1$–$C_4$-alkoxy-substituted alkoxy, alkylthio, alkylsulphinyl, alkylsulphonyl, alkylcarbonyl, alkoxycarbonyl, alkylaminosulphonyl or dialkylaminosulphonyl having in each case 1 to 6 carbon atoms in the alkyl groups, or represents unsubstituted or cyano-, halogen- or $C_1$–$C_4$-alkyl-substituted cycloalkyl, or represents unsubstituted or nitro-, cyano-, carbamoyl-, thiocarbamoyl-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, phenoxy or phenylthio, and—if $R^9$ is different from chlorine or methyl—also represents chlorine or methyl, $R^9$ represents hydrogen, nitro, cyano, carbamoyl, thiocarbamoyl, sulphamoyl, fluorine, bromine, or represents cyano-, halogen- or $C_1$–$C_4$-alkoxy-substituted methyl, or represents unsubstituted or cyano-, halogen- or $C_1$–$C_4$-alkoxy-substituted alkyl having 2 to 6 carbon atoms, or represents unsubstituted or cyano-, halogen- or $C_1$–$C_4$-alkoxy-substituted alkoxy, alkylthio, alkylsulphinyl, alkylsulphonyl, alkylcarbonyl, alkoxycarbonyl, alkylaminosulphonyl or dialkylaminosulphonyl having in each case 1 to 6 carbon atoms in the alkyl groups, or represents unsubstituted or cyano-, halogen- or $C_1$–$C_4$-alkyl-substituted cycloalkyl, or represents unsubstituted or nitro-, cyano-, carbamoyl-, thiocarbamoyl-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, phenoxy or phenylthio, and—if $R^8$ is different from chlorine or methyl—also represents chlorine or methyl, $R^{10}$ represents hydrogen, nitro, cyano, carbamoyl, thiocarbamoyl, sulphamoyl, halogen, or represents unsubstituted or cyano-, halogen- or $C_1$–$C_4$-alkoxy-substituted alkyl, alkoxy, alkylthio, alkylsulphinyl, alkylsulphonyl, alkylcarbonyl, alkoxycarbonyl, alkylaminosulphonyl or dialkylaminosulphonyl having in each case 1 to 6 carbon atoms in the alkyl groups, or represents unsubstituted or cyano-, halogen- or $C_1$–$C_4$-alkyl-substituted cycloalkyl, or represents unsubstituted or nitro-, cyano-, carbamoyl-, thiocarbamoyl-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, phenoxy or phenylthio, $R^{11}$ represents hydrogen, nitro, cyano, carbamoyl, thiocarbamoyl, sulphamoyl, halogen, or represents unsubstituted or cyano-, halogen- or $C_1$–$C_4$-alkoxy-substituted alkyl, alkoxy, alkylthio, alkylsulphinyl, alkylsulphonyl, alkylcarbonyl, alkoxycarbonyl, alkylaminosulphonyl or dialkylaminosulphonyl having in each case 1 to 6 carbon atoms in the alkyl groups, or represents unsubstituted or cyano-, halogen- or $C_1$–$C_4$-alkyl-substituted cycloalkyl, or represents unsubstituted or nitro-, cyano-, carbamoyl-, thiocarbamoyl-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, phenoxy or phenylthio, $R^{12}$ represents hydrogen, nitro, cyano, carbamoyl, thiocarbamoyl, sulphamoyl, halogen, or represents unsubstituted or cyano-, halogen- or $C_1$–$C_4$-alkoxy-substituted alkyl, alkoxy, alkylthio, alkylsulphinyl, alkylsulphonyl, alkylcarbonyl, alkoxycarbonyl, alkylaminosulphonyl or dialkylaminosulphonyl having in each case 1 to 6 carbon atoms in the alkyl groups, or represents unsubstituted or cyano-, halogen- or $C_1$–$C_4$-alkyl-substituted cycloalkyl, or represents unsubstituted or nitro-, cyano-, carbamoyl-, thiocarbamoyl-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, phenoxy or phenylthio, and Q represents oxygen or sulphur.

2. A compound of the formula (I) according to claim 1, wherein $R^1$ represents hydrogen or represents unsubstituted or cyano-, fluorine-, chlorine-, methoxy- or ethoxy-substituted methyl, ethyl, n- or i-propyl, n-, i-, s- or t-butyl, $R^2$ represents hydrogen, or represents unsubstituted or cyano-, fluorine-, chlorine-, methoxy- or ethoxy-substituted methyl, ethyl, n- or i-propyl, n-, i-, s- or t-butyl or represents the grouping —CO—$R^6$, $R^3$ represents unsubstituted or fluorine-, chlorine- or bromine-substituted methyl, ethyl, n- or i-propyl, n-, i-, s- or t-butyl, or represents unsubstituted or fluorine-, chlorine- or bromine-substituted cyclopropyl, cyclobutyl, cyclopentyl or cyclohexyl, $R^4$ represents unsubstituted or cyano-, fluorine-, chlorine-, methoxy- or ethoxy-substituted methyl, ethyl, n- or i-propyl, n-, i-, s- or t-butyl, or represents unsubstituted or cyano-, fluorine-, chlorine-, methyl- or ethyl-substituted cyclopropyl, cyclobutyl, cyclopentyl or cyclohexyl, $R^5$ represents one of the groupings below,

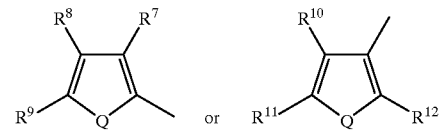

$R^6$ represents hydrogen or represents unsubstituted or cyano-, fluorine-, chlorine-, bromine-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, methylamino, ethylamino, n- or i-propylamino, n-, i-, s- or t-butylamino, dimethylamino or diethylamino, or represents unsubstituted or fluorine-, chlorine-, and/or bromine-substituted ethenyl, propenyl or butenyl, $R^7$ represents hydrogen, nitro, cyano, carbamoyl, thiocarbamoyl, sulphamoyl, fluorine, chlorine, bromine, or represents unsubstituted or cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl, ethylsulphonyl, acetyl, propionyl, n- or i-butyroyl, methoxycarbonyl, ethoxycarbonyl, methylaminosulphonyl, ethylaminosulphonyl, dimethylaminosulphonyl or diethylaminosulphonyl, or represents unsubstituted or cyano-, fluorine-, chlorine-, bromine-, methyl- or ethyl-substituted cyclopropyl, cyclobutyl, cyclopentyl or cyclohexyl, or represents unsubstituted or nitro-, cyano-, carbamoyl-, thiocarbamoyl-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy, difluoromethoxy- or trifluoromethoxy-substituted phenyl, phenoxy or phenylthio, $R^8$ represents hydrogen, nitro, cyano, carbamoyl, thiocarbamoyl, sulphamoyl, fluorine, bromine, or represents cyano-, fluorine-, chlorine-, bromine-, methoxy- or ethoxy-substituted methyl, or represents unsubstituted or cyano-, fluorine, chlorine-, methoxy- or ethoxy-substituted ethyl, n- or i-propyl, n-, i-, s- or t-butyl, or represents unsubstituted or cyano-, fluorine-, chlorine-, methoxy- or ethoxy-substituted methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl, ethylsulphonyl, acetyl, propionyl, n- or i-butyroyl, methoxycarbonyl, ethoxycarbonyl, methylaminosulphonyl, ethylaminosulphonyl, dimethylaminosulphonyl or diethylaminosulphonyl, or represents unsubstituted or cyano-, fluorine-, chlorine-, bromine-, methyl- or ethyl-substituted cyclopropyl, cyclobutyl, cyclopentyl or cyclohexyl, or represents unsubstituted or nitro-, cyano-, carbamoyl-, thiocarbamoyl-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted phenyl, phenoxy or phenylthio, and—if $R^9$ is different from chlorine or methyl—also represents chlorine or methyl, $R^9$ represents hydrogen, nitro, cyano, carbamoyl, thiocarbamoyl, sulphamoyl, fluorine, bromine, or represents cyano-, fluorine-, chlorine-, methoxy- or ethoxy-substituted methyl, or represents unsubstituted or cyano-, fluorine-, chlorine-, methoxy- or ethoxy-substituted ethyl, n- or i-propyl, n-, i-, s- or t-butyl, or represents unsubstituted or cyano-, fluorine-, chlorine-, bromine-, methoxy- or ethoxy-substituted methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl, ethylsulphonyl, acetyl, propionyl, n- or i-butyroyl, methoxycarbonyl, ethoxycarbonyl, methylaminosulphonyl, ethylamino-sulphonyl, dimethylaminosulphonyl or diethylaminosulphonyl, or represents unsubstituted or cyano-, fluorine-, chlorine-, bromine-, methyl- or ethyl-substituted cyclopropyl, cyclobutyl, cyclopentyl or cyclohexyl, or represents unsubstituted or nitro-, cyano-, carbamoyl-, thiocarbamoyl-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted phenyl, phenoxy or phenylthio, and —if $R^8$ is different from chlorine or methyl—also represents chlorine or methyl, $R^{10}$ represents hydrogen, nitro, cyano, carbamoyl, thiocarbamoyl, sulphamoyl, fluorine, chlorine, bromine, or represents unsubstituted or cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl, ethylsulphonyl, acetyl, propionyl, n- or i-butyroyl, methoxycarbonyl, ethoxycarbonyl, methylaminosulphonyl, ethylaminosulphonyl, dimethylaminosulphonyl or diethylaminosulphonyl, or represents unsubstituted or cyano-, fluorine-, chlorine-, bromine-, methyl- or ethyl-substituted cyclopropyl, cyclobutyl, cyclopentyl or cyclohexyl, or represents unsubstituted or nitro-, cyano-, carbamoyl-, thiocarbamoyl-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy, difluoromethoxy- or trifluoromethoxy-substituted phenyl, phenoxy or phenylthio, $R^{11}$ represents hydrogen, nitro, cyano, carbamoyl, thiocarbamoyl, sulphamoyl, fluorine, chlorine, bromine, or represents unsubstituted or cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl, ethylsulphonyl, acetyl, propionyl, n- or i-butyroyl, methoxycarbonyl, ethoxycarbonyl, methylaminosulphonyl, ethylaminosulphonyl, dimethylaminosulphonyl or diethylaminosulphonyl, or represents unsubstituted or cyano-, fluorine-, chlorine-, bromine-, methyl- or ethyl-substituted cyclopropyl, cyclobutyl, cyclopentyl or cyclohexyl, or represents unsubstituted or nitro-, cyano-, carbamoyl-, thiocarbamoyl-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted phenyl, phenoxy or phenylthio, $R^{12}$ represents hydrogen, nitro, cyano, carbamoyl, thiocarbamoyl, sulphamoyl, fluorine, chlorine, bromine, or represents unsubstituted or cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl, ethylsulphonyl, acetyl, propionyl, n- or i-butyroyl, methoxycarbonyl, ethoxycarbonyl, methylaminosulphonyl, ethylaminosulphonyl, dimethylaminosulphonyl or diethylaminosulphonyl, or represents unsubstituted or cyano-, fluorine-, chlorine-, bromine-, methyl- or ethyl-substituted cyclopropyl, cyclobutyl, cyclopentyl or cyclohexyl, or represents unsubstituted or nitro-, cyano-, carbamoyl-, thiocarbamoyl-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted phenyl, phenoxy or phenylthio, and Q represents oxygen or sulphur.

3. A compound of the formula (I) according to claim 1, wherein $R^1$ represents hydrogen, $R^2$ represents hydrogen or represents the grouping —CO—$R^6$, $R^3$ represents unsubstituted or fluorine- or chlorine-substituted methyl, ethyl, n- or i-propyl, or represents unsubstituted or fluorine or chlorine-substituted cyclopropyl, $R^4$ represents unsubstituted or cyano-, fluorine-, chlorine-, methoxy- or ethoxy-substituted methyl, ethyl, n- or i-propyl, or represents unsubstituted or cyano-, fluorine-, chlorine- or methyl-substituted cyclopropyl, $R^5$ represents one of the groupings below,

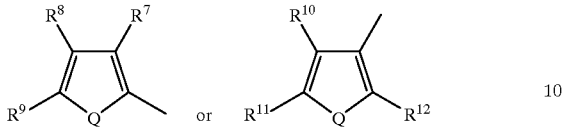

$R^6$ represents hydrogen or represents unsubstituted or cyano-, fluorine-, chlorine-, methoxy- or ethoxy-substituted methyl, ethyl, n- or i-propyl, methoxy or ethoxy, or represents unsubstituted or fluorine- and/or chlorine-substituted ethenyl or propenyl, $R^7$ represents hydrogen, nitro, cyano, carbamoyl, thiocarbamoyl, sulphamoyl, fluorine, chlorine, bromine, or represents unsubstituted or cyano-, fluorine-, chlorine-, methoxy- or ethoxy-substituted methyl, ethyl, n- or i-propyl, methoxy, ethoxy, n- or i-propoxy, methylthio, ethylthio, n- or i-propylthio, methylsulphinyl, ethylsulphinyl, methylsulphonyl, ethylsulphonyl, acetyl, propionyl, methoxycarbonyl, ethoxycarbonyl, or represents unsubstituted or cyano-, fluorine-, chlorine- or methyl-substituted cyclopropyl, or represents unsubstituted or nitro-, cyano-, carbamoyl-, thiocarbamoyl-, fluorine-, chlorine-, bromine-, methyl-, trifluoromethyl-, methoxy-, difluoromethoxy- or trifluoro-methoxy-substituted phenyl, phenoxy or phenylthio, $R^8$ represents hydrogen, nitro, cyano, carbamoyl, thiocarbamoyl, sulphamoyl, fluorine, bromine, or represents unsubstituted or cyano-, fluorine-, chlorine-, methoxy- or ethoxy-substituted ethyl, n- or i-propyl, or represents unsubstituted or cyano-, fluorine-, chlorine-, methoxy- or ethoxy-substituted methoxy, ethoxy, n- or i-propoxy, methylthio, ethylthio, n- or i-propylthio, methylsulphinyl, ethylsulphinyl, methylsulphonyl, ethylsulphonyl, acetyl, propionyl, methoxycarbonyl, ethoxycarbonyl, or represents unsubstituted or cyano-, fluorine-, chlorine- or methyl-substituted cyclopropyl, or represents unsubstituted or nitro-, cyano, carbamoyl-, thiocarbamoyl-, fluorine-, chlorine-, bromine-, methyl-, trifluoromethyl-, methoxy-, difluoromethoxy- or trifluoromethoxy-substituted phenyl, phenoxy or phenylthio, and—if $R^9$ is different from chlorine or methyl—also represents chlorine or methyl, $R^9$ represents hydrogen, nitro, cyano, carbamoyl, thiocarbamoyl, sulphamoyl, fluorine, bromine, or represents unsubstituted or cyano-, fluorine-, chlorine-, methoxy- or ethoxy-substituted ethyl, n- or i-propyl, or represents unsubstituted or cyano-, fluorine-, chlorine-, bromine-, methoxy- or ethoxy-substituted methoxy, ethoxy, n- or i-propoxy, methylthio, ethylthio, n- or i-propylthio, methylsulphinyl, ethylsulphinyl, methylsulphonyl, ethylsulphonyl, acetyl, propionyl, methoxycarbonyl, ethoxycarbonyl, or represents unsubstituted or cyano-, fluorine-, chlorine- or methyl-substituted cyclopropyl, or represents unsubstituted or nitro-, cyano-, carbamoyl-, thiocarbamoyl-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted phenyl, phenoxy or phenylthio, and—if $R^8$ is different from chlorine or methyl—also represents chlorine or methyl, $R^{10}$ represents hydrogen, nitro, cyano, carbamoyl, thiocarbamoyl, sulphamoyl, fluorine, chlorine, bromine, or represents unsubstituted or cyano-, fluorine-, chlorine-, methoxy- or ethoxy-substituted methyl, ethyl, n- or i-propyl, methoxy, ethoxy, n- or i-propoxy, methylthio, ethylthio, n- or i-propylthio, methylsulphinyl, ethylsulphinyl, methylsulphonyl, ethylsulphonyl, acetyl, propionyl, methoxycarbonyl, ethoxycarbonyl, or represents unsubstituted or cyano-, fluorine-, chlorine- or methyl-substituted cyclopropyl, or represents unsubstituted or nitro-, cyano-, carbamoyl-, thiocarbamoyl-, fluorine-, chlorine-, bromine-, methyl-, trifluoromethyl-, methoxy-, difluoromethoxy- or trifluoro-methoxy-substituted phenyl, phenoxy or phenylthio, $R^{11}$ represents hydrogen, nitro, cyano, carbamoyl, thiocarbamoyl, sulphamoyl, fluorine, chlorine, bromine, or represents unsubstituted or cyano-, fluorine-, chlorine-, methoxy- or ethoxy-substituted methyl, ethyl, n- or i-propyl, methoxy, ethoxy, n- or i-propoxy, methylthio, ethylthio, n- or i-propylthio, methylsulphinyl, ethylsulphinyl, methylsulphonyl, ethylsulphonyl, acetyl, propionyl, methoxycarbonyl, ethoxycarbonyl, or represents unsubstituted or cyano-, fluorine-, chlorine- or methyl-substituted cyclopropyl, or represents unsubstituted or nitro-, cyano-, carbamoyl-, thiocarbamoyl-, fluorine-, chlorine-, bromine-, methyl-, trifluoromethyl-, methoxy-, difluoromethoxy- or trifluoro-methoxy-substituted phenyl, phenoxy or phenylthio, $R^{12}$ represents hydrogen, nitro, cyano, carbamoyl, thiocarbamoyl, sulphamoyl, fluorine, chlorine, bromine, or represents unsubstituted or cyano-, fluorine-, chlorine-, methoxy- or ethoxy-substituted methyl, ethyl, n- or i-propyl, methoxy, ethoxy, n- or i-propoxy, methylthio, ethylthio, n- or i-propylthio, methylsulphinyl, ethylsulphinyl, methylsulphonyl, ethylsulphonyl, acetyl, propionyl, methoxycarbonyl, ethoxycarbonyl, or represents unsubstituted or cyano-, fluorine-, chlorine- or methyl-substituted cyclopropyl, or represents unsubstituted or nitro-, cyano-, carbamoyl-, thiocarbamoyl-, fluorine-, chlorine-, bromine-, methyl-, trifluoromethyl-, methoxy-, difluoromethoxy- or trifluoro-methoxy-substituted phenyl, phenoxy or phenylthio, and Q represents oxygen or sulphur.

4. A herbicidal composition, comprising one or more compound of the formula (I) according to claim 1 and one or more ingredients selected from the group consisting of extenders and surfactants.

5. A method for controlling weeds, comprising the step of allowing an effective amount of a compound of the formula (I) according to claim 1 to act on the weeds or their habitat.

6. A 2,4-diamino-1,3,5-triazine according to claim 1, wherein $R^8$ represents hydrogen, nitro, cyano, carbamoyl, thiocarbamoyl, sulphamoyl, fluorine, or represents cyano-, halogen- or $C_1$–$C_4$-alkoxy-substituted methyl, or represents unsubstituted or cyano-, halogen- or $C_1$–$C_4$-alkoxy-substituted alkyl having 2 to 6 carbon atoms, or represents unsubstituted or cyano-, halogen- or $C_1$–$C_4$-alkoxy-substituted alkoxy, alkylthio, alkylsulphinyl, alkylsulphonyl, alkylcarbonyl, alkoxycarbonyl, alkylaminosulphonyl or dialkylaminosulphonyl having in each case 1 to 6 carbon atoms in the alkyl groups, or represents unsubstituted or cyano-, halogen- or $C_1$–$C_4$-alkyl-substituted cycloalkyl, or represents unsubstituted or nitro-, cyano-, carbamoyl-, thiocarbamoyl-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, phenoxy or phenylthio, and—if $R^9$ is different from chlorine, bromine, methyl—also represents chlorine, bromine or methyl, and $R^9$ represents hydrogen, nitro, cyano, carbamoyl, thiocarbamoyl, sulphamoyl, fluorine, or represents cyano-, halogen- or $C_1$–$C_4$-alkoxy-substituted methyl, or represents unsubstituted or cyano-, halogen- or $C_1$–$C_4$-alkoxy-substituted alkyl having 2 to 6 carbon atoms, or represents unsubstituted or cyano-, halogen- or $C_1$–$C_4$-alkoxy-substituted alkoxy, alkylthio, alkylsulphinyl, alkylsulphonyl, alkylcarbonyl, alkoxycarbonyl, alkylaminosulphonyl or dialkylaminosulphonyl having in each case 1 to 6 carbon atoms in the alkyl groups, or represents unsubstituted or cyano-, halogen- or $C_1$–$C_4$-alkyl-substituted cycloalkyl, or represents unsubstituted or nitro-, cyano-, carbamoyl-, thiocarbamoyl-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, phenoxy or phenylthio, and—if $R^8$ is different from chlorine, bromine or methyl—also represents chlorine, bromine or methyl;

with the proviso that when $R^8$ is bromine $R^9$ is other than an unsubstituted alkylthio having 1 carbon atom in the alkyl group.

7. A 2,4-diamino-1,3,5-triazine according to claim 1, wherein $R^4$ represents unsubstituted or cyano-, halogen- or $C_1$–$C_4$-alkoxy-substituted alkyl having 1 to 6 carbon atoms.

8. A 2,4-diamino1,3,5-triazine of the formula (I)

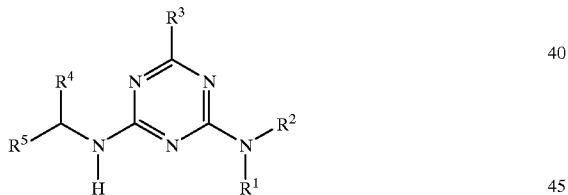

(I)

wherein
R¹ represents hydrogen or represents unsubstituted or cyano-, halogen- or $C_1$–$C_4$-alkoxy-substituted alkyl having 1 to 6 carbon atoms, R² represents hydrogen, or represents unsubstituted or cyano-, halogen- or $C_1$–$C_4$-alkoxy-substituted alkyl having 1 to 6 carbon atoms or represents the grouping —CO—R⁶, R³ represents unsubstituted or hydroxyl-, halogen- or $C_1$–$C_4$-alkoxy-substituted alkyl having 1 to 6 carbon atoms, or represents unsubstituted or halogen- or $C_1$–$C_4$-alkoxy-substituted alkenyl or alkinyl having in each case 2 to 6 carbon atoms, or represents unsubstituted or halogen- or $C_1$–$C_4$-alkyl-substituted cycloalkyl having 3 to 6 carbon atoms, R⁴ represents unsubstituted or cyano-, halogen- or $C_1$–$C_4$-alkoxy-substituted alkyl having 1 to 6 carbon atoms, or represents unsubstituted or cyano-, halogen- or $C_1$–$C_4$-alkyl-substituted cycloalkyl having 3 to 6 carbon atoms, R⁵ represents one of the groupings below,

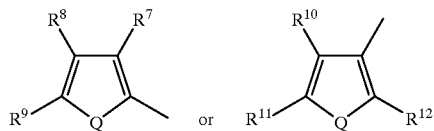

R⁶ represents hydrogen or represents unsubstituted or cyano-, halogen- or $C_1$–$C_4$-alkoxy-substituted alkyl, alkoxy, alkylamino or dialkylamino having 1 to 6 carbon atoms in the alkyl groups or represents unsubstituted or halogen-substituted alkenyl having 2 to 6 carbon atoms, R⁷ represents hydrogen, nitro, cyano, carbamoyl, thiocarbamoyl, sulphamoyl, halogen, or represents unsubstituted or cyano-, halogen- or $C_1$–$C_4$-alkoxy-substituted alkyl, alkoxy, alkylthio, alkylsulphinyl, alkylsulphonyl, alkylcarbonyl, alkoxycarbonyl, alkylaminosulphonyl or dialkylaminosulphonyl having 1 to 6 carbon atoms in the alkyl groups, or represents unsubstituted or cyano-, halogen- or $C_1$–$C_4$-alkyl-substituted cycloalkyl, or represents unsubstituted or nitro-, cyano-, carbamoyl-, thiocarbamoyl-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, phenoxy or phenylthio, R⁸ represents hydrogen, nitro, cyano, carbamoyl, thiocarbamoyl, sulphamoyl, fluorine, bromine, chlorine or represents cyano-, halogen- or $C_1$–$C_4$-alkoxy-substituted methyl, or represents unsubstituted or cyano-, halogen- or $C_1$–$C_4$-alkoxy-substituted alkyl having 2 to 6 carbon atoms, or represents unsubstituted or cyano-, halogen- or $C_1$–$C_4$-alkoxy-substituted alkoxy, alkylthio, alkylsulphinyl, alkylsulphonyl, alkylcarbonyl, alkoxycarbonyl, alkylaminosulphonyl or dialkylaminosulphonyl having 1 to 6 carbon atoms in the alkyl groups, or represents unsubstituted or cyano-, halogen- or $C_1$–$C_4$-alkyl-substituted cycloalkyl, or represents unsubstituted or nitro-, cyano-, carbamoyl-, thiocarbamoyl-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, phenoxy or phenylthio, R⁹ represents hydrogen, nitro, cyano, carbamoyl, thiocarbamoyl, sulphamoyl, fluorine, bromine, chlorine or unsubstituted or cyano-, halogen- or $C_1$–$C_4$-alkoxy-substituted methyl, or represents unsubstituted or cyano-, halogen- or $C_1$–$C_4$-alkoxy-substituted alkyl having 2 to 6 carbon atoms, or represents unsubstituted or cyano-, halogen- or $C_1$–$C_4$-alkoxy-substituted alkoxy, alkylthio, alkylsulphinyl, alkylsulphonyl, alkylcarbonyl, alkoxycarbonyl, alkylaminosulphonyl or dialkylaminosulphonyl having 1 to 6 carbon atoms in the alkyl groups, or represents unsubstituted or cyano-, halogen- or $C_1$–$C_4$-alkyl-substituted cycloalkyl, or represents unsubstituted or nitro-, cyano-, carbamoyl-, thiocarbamoyl-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, phenoxy or phenylthio, R¹⁰ represents hydrogen, nitro, cyano, carbamoyl, thiocarbamoyl, sulphamoyl, halogen, or represents unsubstituted or cyano-, halogen- or $C_1$–$C_4$-alkoxy-substituted alkyl, alkoxy, alkylthio, alkylsulphinyl, alkylsulphonyl, alkylcarbonyl, alkoxycarbonyl, alkylaminosulphonyl or dialkylaminosulphonyl having 1 to 6 carbon atoms in the alkyl groups, or represents unsubstituted or cyano-, halogen- or $C_1$–$C_4$-alkyl-substituted cycloalkyl, or represents unsubstituted or nitro-, cyano-, carbamoyl-, thiocarbamoyl-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, phenoxy or phenylthio, $R^{11}$ represents hydrogen, nitro, cyano, carbamoyl, thiocarbamoyl, sulphamoyl, halogen, or represents unsubstituted or cyano-, halogen- or $C_1$–$C_4$-alkoxy-substituted alkyl, alkoxy, alkylthio, alkylsulphinyl, alkylsulphonyl, alkylcarbonyl, alkoxycarbonyl, alkylaminosulphonyl or dialkylaminosulphonyl having 1 to 6 carbon atoms in the alkyl groups, or represents unsubstituted or cyano-, halogen- or $C_1$–$C_4$-alkyl-substituted cycloalkyl, or represents unsubstituted or nitro-, cyano-, carbamoyl-, thiocarbamoyl-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, phenoxy or phenylthio, $R^{12}$ represents hydrogen, nitro, cyano, carbamoyl, thiocarbamoyl, sulphamoyl, halogen, or represents unsubstituted or cyano-, halogen- or $C_1$–$C_4$-alkoxy-substituted alkyl, alkoxy, alkylthio, alkylsulphinyl, alkylsulphonyl, alkylcarbonyl, alkoxycarbonyl, alkylaminosulphonyl or dialkylaminosulphonyl having 1 to 6 carbon atoms in the alkyl groups, or represents unsubstituted or cyano-, halogen- or $C_1$–$C_4$-alkyl-substituted cycloalkyl, or represents unsubstituted or nitro-, cyano-, carbamoyl-, thiocarbamoyl-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, phenoxy or phenylthio, and Q represents oxygen or sulphur;

with the proviso that if $R^9$ is chlorine or methyl then $R^8$ is other than chlorine or methyl.

9. A 2,4-diamino-1,3,5-triazine according to claim 8, wherein:

when $R^7$ is hydrogen and $R^8$ is methyl, then $R^9$ is other than chlorine, bromine or methyl; when $R^7$ is hydrogen and $R^8$ bromine, then $R^9$ is other than bromine or methylthio; and when $R^7$ is hydrogen and $R^8$ is chlorine, then $R^9$ is other than chlorine.

10. A 2,4-diamino-1,3,5-triazine according to claim 8, wherein at least one of $R^8$ and $R^9$ is hydrogen.

11. A 2,4-diamino-1,3,5-triazine according to claim 10, wherein $R^3$ is methyl.

12. A 2,4-diamino1,3,5-triazine according to claim 7, wherein:

$R^4$ represents unsubstituted or cyano-, halogen- or $C_1$–$C_4$-alkoxy-substituted alkyl having 1 to 6 carbon atoms, $R^7$ represents hydrogen, nitro, cyano, carbamoyl, thiocarbamoyl, sulphamoyl, halogen, or represents unsubstituted or cyano-, halogen- or $C_1$–$C_4$-alkoxy-substituted alkyl, alkoxy, alkylthio, alkylsulphinyl, alkylsulphonyl, alkylcarbonyl, alkoxycarbonyl, alkylaminosulphonyl or dialkylaminosulphonyl having 1 to 6 carbon atoms in the alkyl groups, $R^8$ represents hydrogen, nitro, cyano, carbamoyl, thiocarbamoyl, sulphamoyl, fluorine, bromine, chlorine or represents unsubstituted or cyano-, halogen- or $C_1$–$C_4$-alkoxy-substituted methyl, or represents unsubstituted or cyano-, halogen- or $C_1$–$C_4$-alkoxy-substituted alkyl having 2 to 6 carbon atoms, or represents unsubstituted or cyano-, halogen- or $C_1$–$C_4$-alkoxy-substituted alkoxy, alkylthio, alkylsulphinyl, alkylsulphonyl, alkylcarbonyl, alkoxycarbonyl, alkylaminosulphonyl or dialkylaminosulphonyl having 1 to 6 carbon atoms in the alkyl groups, $R^9$ represents hydrogen, nitro, cyano, carbamoyl, thiocarbamoyl, sulphamoyl, fluorine, bromine, chlorine or unsubstituted or cyano-, halogen- or $C_1$–$C_4$-alkoxy-substituted methyl, or represents unsubstituted or cyano-, halogen- or $C_1$–$C_4$-alkoxy-substituted alkyl having 2 to 6 carbon atoms, or represents unsubstituted or cyano-, halogen- or $C_1$–$C_4$-alkoxy-substituted alkoxy, alkylthio, alkylsulphinyl, alkylsulphonyl, alkylcarbonyl, alkoxycarbonyl, alkylaminosulphonyl or dialkylaminosulphonyl having 1 to 6 carbon atoms in the alkyl groups, $R^{10}$ represents hydrogen, nitro, cyano, carbamoyl, thiocarbamoyl, sulphamoyl, halogen, or represents unsubstituted or cyano-, halogen- or $C_1$–$C_4$-alkoxy-substituted alkyl, alkoxy, alkylthio, alkylsulphinyl, alkylsulphonyl, alkylcarbonyl, alkoxycarbonyl, alkylaminosulphonyl or dialkylaminosulphonyl having 1 to 6 carbon atoms in the alkyl groups, $R^{11}$ represents hydrogen, nitro, cyano, carbamoyl, thiocarbamoyl, sulphamoyl, halogen, or represents unsubstituted or cyano-, halogen- or $C_1$–$C_4$-alkoxy-substituted alkyl, alkoxy, alkylthio, alkylsulphinyl, alkylsulphonyl, alkylcarbonyl, alkoxycarbonyl, alkylaminosulphonyl or dialkylaminosulphonyl having 1 to 6 carbon atoms in the alkyl groups, and $R^{12}$ represents hydrogen, nitro, cyano, carbamoyl, thiocarbamoyl, sulphamoyl, halogen, or represents unsubstituted or cyano-, halogen- or $C_1$–$C_4$-alkoxy-substituted alkyl, alkoxy, alkylthio, alkylsulphinyl, alkylsulphonyl, alkylcarbonyl, alkoxycarbonyl, alkylaminosulphonyl or dialkylaminosulphonyl having 1 to 6 carbon atoms in the alkyl groups.

13. A 2,4-diamino-1,3,5-triazine according to claim 12, wherein:

$R^1$ represents hydrogen, $R^2$ represents hydrogen or represents the grouping —CO—$R^6$, $R^3$ represents in each case unsubstituted fluorine-, chlorine- or bromine-substituted methyl, ethyl, n- or i-propyl, n-, i-, s- or t-butyl, $R^4$ represents methyl or ethyl, $R^6$ represents methyl or ethyl, and $R^7$, $R^8$, $R^9$, $R^{10}$, $R^{11}$, and $R^{12}$ each independently represents hydrogen, fluorine, chlorine, bromine, or methyl.

14. A 2,4-diamino-1,3,5-triazine according to claim 7, wherein $R^5$ represents:

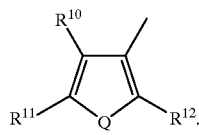

15. A 2,4-diamino-1,3,5-triazine according to claim 8, wherein $R^3$ represents unsubstituted or halogen-substituted alkyl having 1 to 6 carbon atoms, or represents unsubstituted or halogen-substituted cycloalkyl having 3 to 6 carbon atoms.

* * * * *